US006617437B1

(12) United States Patent
Matteucci et al.

(10) Patent No.: US 6,617,437 B1
(45) Date of Patent: *Sep. 9, 2003

(54) PYRIMIDINE DERIVATIVES FOR LABELED BINDING PARTNERS

(75) Inventors: Mark Matteucci, Burlingame, CA (US); Robert J. Jones, Millbrae, CA (US); Kuei-Ying Lin, Fremont, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/468,454

(22) Filed: Dec. 21, 1999

Related U.S. Application Data

(63) Continuation of application No. 08/436,991, filed on May 8, 1995, now Pat. No. 6,005,096, which is a continuation of application No. 08/123,505, filed on Sep. 17, 1993, now Pat. No. 5,502,177.

(51) Int. Cl.[7] ............................................ C07H 21/00

(52) U.S. Cl. .................... 536/23.1; 536/26.6; 536/28.5; 536/28.51; 536/28.52; 514/44; 435/91.2

(58) Field of Search .......................... 435/91.2; 514/44; 536/28.5–52, 23.1, 26.6; 544/242

(56) References Cited

U.S. PATENT DOCUMENTS

| | | | |
|---|---|---|---|
| 3,316,255 A | 4/1967 | Takamizawa et al. | 544/34 |
| 3,583,298 A | 6/1971 | Van Swearingen | 95/1 |

(List continued on next page.)

FOREIGN PATENT DOCUMENTS

| | | |
|---|---|---|
| EP | 0 318 245 A2 | 5/1989 |
| EP | 0 541 153 A1 | 5/1993 |
| JP | 62-059293 A2 | 3/1987 |
| WO | WO 88/07542 | 10/1988 |
| WO | WO 89/12061 | 12/1989 |
| WO | WO 92/08719 | 5/1992 |
| WO | WO 93/06245 | 4/1993 |
| WO | WO 94/24144 | 10/1994 |

OTHER PUBLICATIONS

Jones et al., "Synthesis and Binding Properties of Pyrimidine Oligodeoxy–nucleoside Analogs Containing Neutral Phosphodiester Replacements: The Formacetal and 3'–Thioformacetal Internucleoside Linkages," *Journal of Organic Chemistry*, 58(11), 2983–2991 (May 21, 1993).*

(List continued on next page.)

*Primary Examiner*—Deborah D. Carr
*Assistant Examiner*—L E Crane
(74) *Attorney, Agent, or Firm*—Woodcock Washburn LLP

(57) ABSTRACT

Compounds having particular interest as labels and various novel uses in diagnostics and therapeutics are provided which have structure (1)

(1)

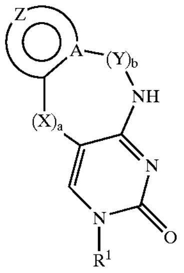

wherein $R^1$ is a binding partner, a linker or H;

a and b are 0 or 1, provided that the total of a and b is 0 or 1;

A is N or C;

X is S, O, —C(O)—, NH or $NCH_2R^6$;

Y is —C(O)—;

Z is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, 2 N ring heteroatoms separated by a carbon atom, or 3 N ring heteroatoms at least two of which are separated by a carbon atom, and wherein the aryl or heteroaryl ring carbon atoms are unsubstituted with other than H or at least 1 nonbridging ring carbon atom is substituted with $R^6$ or =O;

$R^6$ is independently H, $C_1$–$C_6$ alkyl, $C_2$–$C_6$ alkeny, $C_2$–$C_6$ alkynyl, $NO_2$, $N(R^3)_2$, C≡N or halo, or an $R^6$ is taken together with an adjacent $R^6$ to complete a ring containing 5 or 6 ring atoms;, $R^3$ is a protecting group or H; and tautomers, solvates and salts thereof;

and provided that where a is 0, b is 1, and $R^1$ is

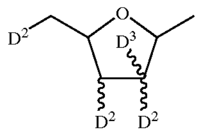

in which $D^2$ is independently hydroxyl, blocked hydroxyl, mono, di or triphosphate, or an oligodeoxyribonucleotide otherwise containing only the bases A, G, T and C; and $D^3$ is H or OH;

then Z is not unsubstituted phenyl.

Also provided are novel intermediates and methods for the preparation and use of the structure (1) compounds.

47 Claims, 16 Drawing Sheets

U.S. PATENT DOCUMENTS

| | | | | | |
|---|---|---|---|---|---|
| 3,706,748 A | | 12/1972 | Rosenfeld et al. | 544/243 |
| 4,169,201 A | | 9/1979 | Kiss | 544/313 |
| 4,396,623 A | | 8/1983 | Shealy et al. | 424/251 |
| 4,746,352 A | | 5/1988 | Wenger et al. | 71/90 |
| 4,879,214 A | | 11/1989 | Kornher et al. | 8/10.89 |
| 5,043,272 A | | 8/1991 | Hartley | 435/91 |
| 5,047,533 A | | 9/1991 | Reist et al. | 544/244 |
| 5,049,551 A | | 9/1991 | Koda et al. | 514/50 |
| 5,106,727 A | | 4/1992 | Hartley et al. | 435/6 |
| 5,112,736 A | | 5/1992 | Caldwell et al. | 435/6 |
| 5,130,238 A | | 7/1992 | Malek et al. | 435/91 |
| 5,130,427 A | | 7/1992 | Alexander et al. | 544/182 |
| 5,142,051 A | | 8/1992 | Holy et al. | 544/243 |
| 5,145,960 A | | 9/1992 | Zahler et al. | 544/310 |
| 5,169,766 A | | 12/1992 | Schuster et al. | 435/91 |
| 5,169,842 A | | 12/1992 | Lobberding et al. | 514/86 |
| 5,194,370 A | | 3/1993 | Berninger et al. | 435/6 |
| 5,208,221 A | | 5/1993 | Kim et al. | 514/81 |
| 5,232,830 A | | 8/1993 | Van Ness | 435/6 |
| 5,502,177 A | * | 3/1996 | Matteucci et al. | 536/26.6 |
| 5,763,588 A | * | 6/1998 | Matteucci et al. | 536/22.1 |
| 6,005,096 A | * | 12/1999 | Matteucci et al. | 536/26.6 |

OTHER PUBLICATIONS

Bernier et al., "Extension of the Nenitzescu Reaction to a Cyclic Enamino Ketone. One Step Synthesis of 6–Hydroxy–9H–pyrimido[4,5–b]indole–2,4–dione," *J. Org. Chem.*, 1981, 46, 4197–4198.*

Fenner et al., "Synthesis and Reactivity of 1,5–Dihydro–5–Thiaflavines," *Liebigs Ann. Chem.*, 1978, 193–213.*

Froehler et al., "Oligonucleotides Derived from 5–(1–Propynyl)–2'–O–Allyl–Uridine and 5–(1–Propynyl)–2'–O–Allyl–Cytidine: Synthesis and RNA Duplex Formation," *Tetra. Lett.*, 1993, 34(6), 1003–1006.*

Milligan et al., "Current Concepts in Antisense Drug Design," *J. Med. Chem.*, 1993 36(14), 1923–1937.*

Palmer et al., "Potential Antitumor Agents. 54. Chromophore Requirements for in Vivo Antitumor Activity among the General Class of Linear Tricyclic Carboxamides," *J. Med. Chem.*, 1988, 31, 707–712.*

Prober et al., "A System for Rapid DNA Sequencing with Fluorescent Chain–Terminating Dideoxynucleotides," *Science*, 1987, 238, 336–341.*

Stein et al., "Oligodeoxynucleotides as Inhibitors of Gene Expression: A Review," *Cancer Res.*, 1988, 48, 2659–2668.*

Dziewiszek et al., "Derivatives of 1–(2–deoxy–2–fluoro–beta–D–arabinofuranosyl)–5–P henyluracil and 5–Benzyluracil. Synthesis and Biological Properties," *Nucleosides Nucleotides*, 1994, 13(1–3), 77–94.*

Jousseaume et al., "(4+2) Cycloadditions of Acetylenic Organotins: Synthetic Applications of Polyfunctional Cyclic Vinyltins," *Tetrahedron*, 1989, 45(4), 1145–1154.*

March, *Advanced Organic Chemistry*, 2nd Edition, McGraw–Hill, Inc., 1977, p. 216.*

Sato et al., "Synthesis of 9H–Pyrimido [4,5–b]indole Derivatives (translated)," *Yakugaku Zasshi*, 1970, 90(5), 618–628.

Silverstein et al., in "Ultraviolet Spectrometry," *Spectrometric Identification of Organic Compounds*, 4th Edition, John Wiley & Sons, 1981, Ch. 6, 305–308 and 321–330.

Tong et al., Huagong Xuebao, *J. Chem. Industry Engineering*, 1986, 3, 329–341.

Wehry, in *Practical Fluorescence*, 2nd Edition, Guilbault, G.G. (ed.), Marcel Dekker, Inc., 1990, 166–173.

Willard et al., "Fluoresence and Phosphorescence Spectrophotometry," in *Instrumental Methods of Analysis*, 6th Edition, D. Van Nostrand Company, 1981, Ch. 4, 105–108.

* cited by examiner

Diazine

Triazine 2-pyridone

4-Pyridone

Phenopyrroline

Pyridinopyrroline

Phenothiazine and Phenoxazine

Phenoxazine

A: $Ac_2O$/Pyridine;
B: 2-mesitylsulfonyl chloride/
4-dimethylaminopyridine/TEA/$CH_2Cl_2$;
C: corresponding 2-aminophenol; DBU
D: $NH_3/CH_3OH$ Naphthyloxazine D: $NH_3/CH_3OH$;
E: 10 eq. KF/ethanol, refluxed;
F: DMT-Cl/pyridine Oxadiazine Oxadiazine

PYRIMIDINE DERIVATIVES FOR LABELED BINDING PARTNERS

This Application: is a continuation of U.S. application Ser. No. 08/436,991 filed May 8, 1995, now U.S. Pat. No. 6,005,096, which is a divisional of application Ser. No. 08/123,505 filed Sep. 17, 1993, now U.S. Pat. No. 5,502, 177.

BACKGROUND OF THE INVENTION

This invention relates to the field of labels, particularly labels for diagnostic use. In particular, it relates to oligonucleotides that are modified to enhance the binding affinity of the oligonucleotides for complementary sequences and that in addition bear a readily detectable characteristic.

Sequence specific binding of oligonucleotides both to single stranded RNA and DNA and to duplex DNA is widely known. This phenomenon has been harnessed for a great variety of diagnostic, preparative and therapeutic purposes. Previously, one objective of research in this field has been to increase the affinity of such oligonucleotides for their complementary sequences. For example, Froehler et al. have described oligonucleotides containing 5-substituted pyrimidine bases that substantially increase the Tm for oligonucleotide binding to complementary bases (International Publication No. 92/10115).

Fluorescent cytosine derivatives are known for use in preparing labeled DNA probes. See Inoue et al., Jpn Kokai JP 62059293, (1987). In addition, fluorescent labeled nucleotides have been employed in DNA sequencing. See Prober et al., "Science" 238:336–341 (1987).

1,3-Dihydro-2H-imidazo[4,5-b]-quinolin-2-one derivatives as phosphodiesterase inhibitors are disclosed by Raeymaekers et al. (EP 541,153).

OBJECTS OF THE INVENTION

An object of this invention is to increase the affinity of oligonucleotides for their complementary sequences.

Another object of this invention is to provide improved detectable labels for use in diagnostic assays.

A further object of this invention is to enhance diagnostic assays which employ oligonucleotides.

A still further object of this invention is to improve the therapeutic efficacy of oligonucleotides.

These and other objects of the invention will be apparent from consideration of the specification as a whole.

Structural Formulas

Structural formulas are designated as parenthetical numerals. It will be understood that designation of aromaticity with respect to carbocycles and heterocycles herein includes any highly resonant unsaturated ring structures Alternatively, placement of double bonds, where indicated, represents one potential structure for the depicted compound but will be understood to include other resonant states of the compound as well as protonated and charged species, only one of which may be shown.

SUMMARY OF THE INVENTION

In accordance with the objects, provided herein is a compound having the structure (1)

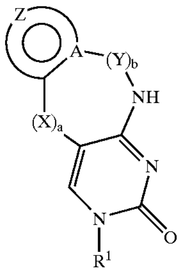

wherein $R^1$ is a binding partner, a linker or H;

a and b are 0 or 1, provided that the total of a and b is 0 or 1;

A is N or C;

X is S, O, —C(O)—, NH or $NCH_2R^6$;

Y is —C(O)—,

Z is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, 2 N ring heteroatoms separated by a carbon atom, or 3 N ring heteroatoms at least two of which are separated by a carbon atom, and wherein the aryl or heteroaryl ring carbon atoms are unsubstituted with other than H or at least 1 nonbridging ring carbon atom is substituted with $R^6$ or ═O;

$R^3$ is a protecting group or H;

$R^6$ is independently H, $C_1$–$C_6$ alkyl, $C_2$–$C_6$ alkenyl, $C_2$–$C_6$ alkynyl, $NO_2$, $N(R^3)_2$, C≡N or halo, or an $R^6$ is taken together with an adjacent $R^6$ to complete a ring containing 5 or 6 ring atoms, and tautomers, solvates and salts thereof; and provided that where a is 0, b is 1, and $R^1$ is

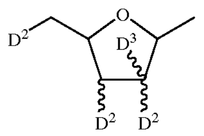

in which $D^2$ is independently hydroxyl, blocked hydroxyl, mono, di or triphosphate, or an oligodeoxyribonucleotide otherwise containing only the bases A, G, T and C; and $D^3$is H or OH;

then Z is not unsubstituted phenyl.

When the binding partner $R^1$ is an oligomer, embodiments of the compounds of this invention have structure (8)

(8)

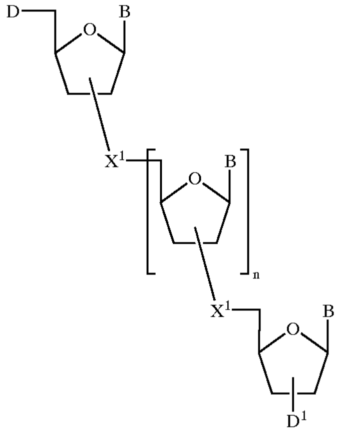

wherein

D is OH or blocked OH;

$D^1$ is an oligonucleotide coupling group or OH $X^1$ is independently a phosphodiester linkage or a phosphodiester substitute linkage bonded to the 2' or 3' position of a furanose ring and the remaining 2' or 3' position is substituted with $R^{21}$;

$R^{21}$ is H, OH, F, —O-alkyl ($C_1$–$C_{12}$), —S-alkyl ($C_1$–$C_{12}$), $OC_3H_5$, or $SC_3H_5$;

n is an integer from 0 to 98; and

B is a purine or pyrimidine base or analogue thereof provided that at least one B has the structure (30)

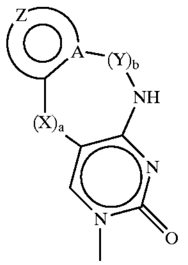

wherein a, b, A, X, Y, Z, and the proviso are the same as for structure (1).

The compounds of structure (1) are made through several novel intermediates. The 4-pyridones are obtained from an intermediate having structure (2)

(2)

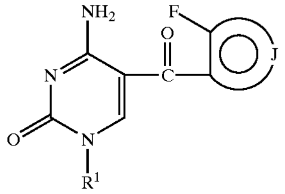

wherein $R^1$ is H or a linker group;

J is an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, or 2 N ring heteroatoms separated by a carbon atom, and wherein the aryl or heteroaryl ring carbon atoms are unsubstituted with other than H or at least 1 nonbridging ring carbon atom is substituted with $R^6$; and $R^6$ is defined above;

and tautomers, salts and solvates thereof.

The 2-pyridones are synthesized from the intermediates of structures (3) and (6):

(3)

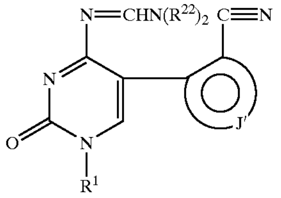

wherein $R^1$ is H or a linker group;

$R^{22}$ is $C_1$–$C_3$ alkyl; and

J' is an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, or 2 N ring heteroatoms separated by a carbon atom, and wherein the aryl or heteroaryl ring carbon atoms are unsubstituted with other than H or at least 1 nonbridging ring carbon atom is substituted with $C_1$–$C_6$ alkyl, $C_2$–$C_6$ alkenyl, $C_2$–$C_6$ alkynyl, $NO_2$, $N(R^3)_2$, or halo;

$R^3$ is a protecting group or H;

and tautomers, solvates and salts thereof.

(6)

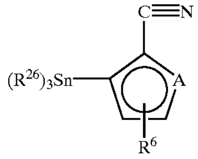

wherein

A is independently S, O, N or $CR^6$;

$R^6$ is defined above; and $R^{26}$ is $C_1$–$C_4$ alkyl; and tautomers, salts and solvates thereof.

Phenoxazines and oxadiazines also are made from novel intermediate (5), as are pyridinopyrrolines, thiazines and oxazines.

(5)

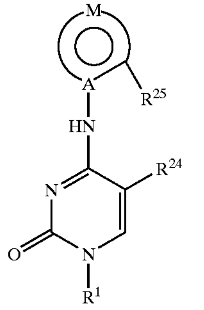

wherein $R^1$ is H or a linker group;

$R^{24}$ is independently halo or $C_1$–$C_2$ haloalkyl;

$R^{25}$ is independently —SH, —OH, =S or =O;

A is independently N or C; and

M, taken together with the radical —A—C(—$R^{25}$), completes an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, 2 N ring heteroatoms separated by a carbon atom, or 3 N ring heteroatoms at least two of which are separated by a carbon atom, and wherein the aryl or heteroaryl ring carbon atoms are unsubstituted with other than H or at least 1 nonbridging ring carbon atom is substituted with $R^6$; and $R^6$ is defined above, and tautomers, solvates and salts thereof.

The phenopyrrolines are made by the use of the intermediate of structure (4)

(4)

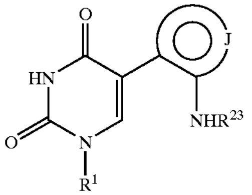

wherein $R^1$ is H or a linker group;

J is an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, or 2 N ring heteroatoms separated by a carbon atom, and wherein the aryl or heteroaryl ring carbon atoms are unsubstituted with other than H or at least 1 nonbridging ring carbon atom is substituted with $R^6$; and $R^6$ is defined above;

$R^{23}$ is a protecting group;

and tautomers, salts and solvates thereof.

BRIEF DESCRIPTION OF THE DRAWINGS

In the drawings $pR^1$ refers to $R^1$ groups in which the hydroxyl groups are protected, e.g. by acetyl substitution, and the remaining substituents are defined above. Ordinarily, the schemes of FIGS. 1–10 are carried out with $R^1$ being a linker group or H; optional covalent bonding to polymer is accomplished after the steps shown in the schemes, as is more fully described below.

FIGS. 1–10 show methods for the diazine (FIG. 1), triazine (FIG. 2), 2-pyridone (FIG. 3), 4-pyridone (FIG. 4), phenopyrroline (FIG. 5), pyridinopyrroline (FIG. 6), thiazine and oxazine (FIG. 7), phenoxazine (FIGS. 8A–8B), naphthyloxazine (FIG. 9) and oxadiazine (FIGS. 10A and 10B) compounds of this invention.

DETAILED DESCRIPTION OF THE INVENTION

Figure 1:
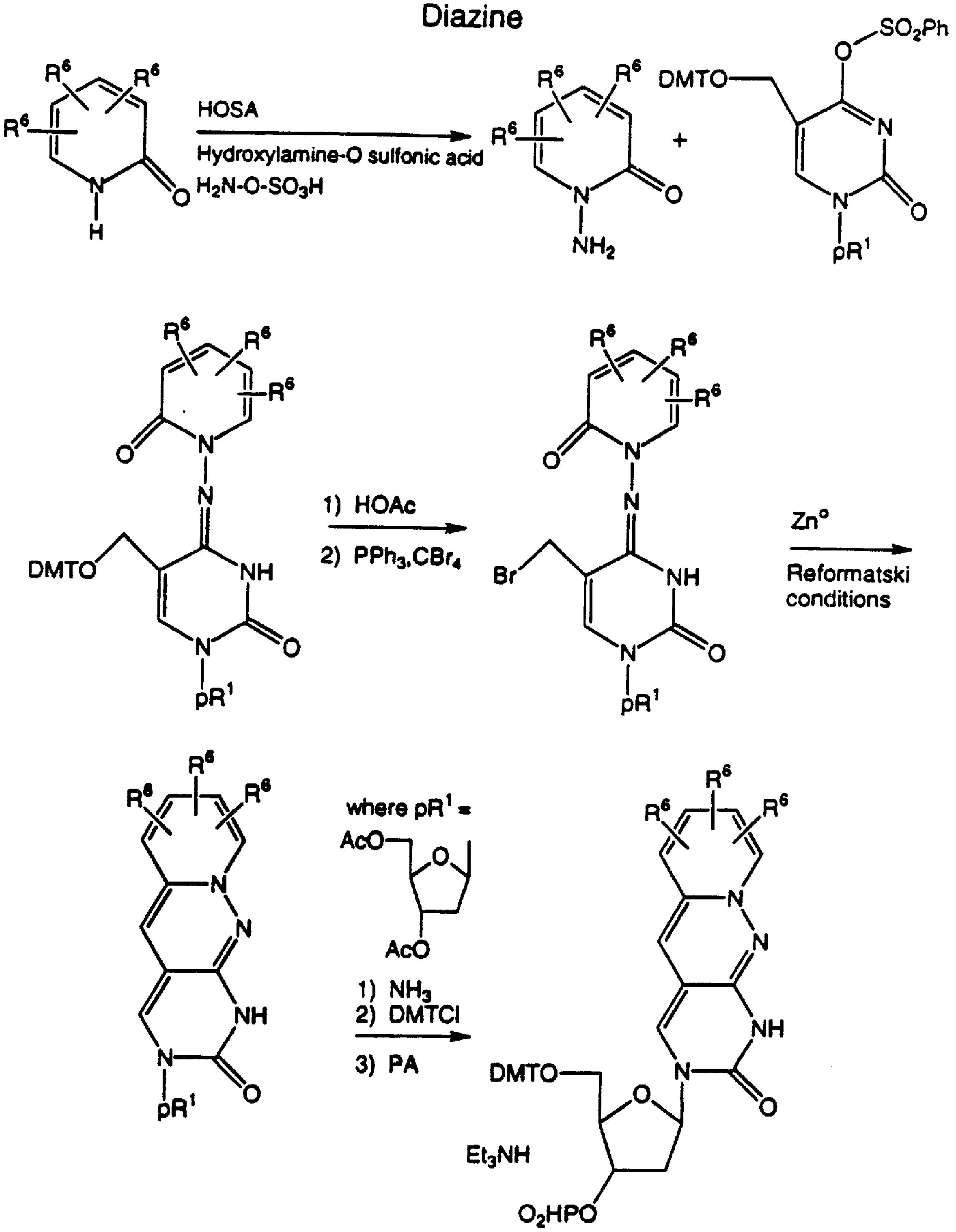
FIGS. 1–10 depict, respectively, methods for the preparation of compounds of this invention. For convenience, the schemes are named for the entire or partial ring structure fused to the pyrimidinyl radical.
Figure 2:
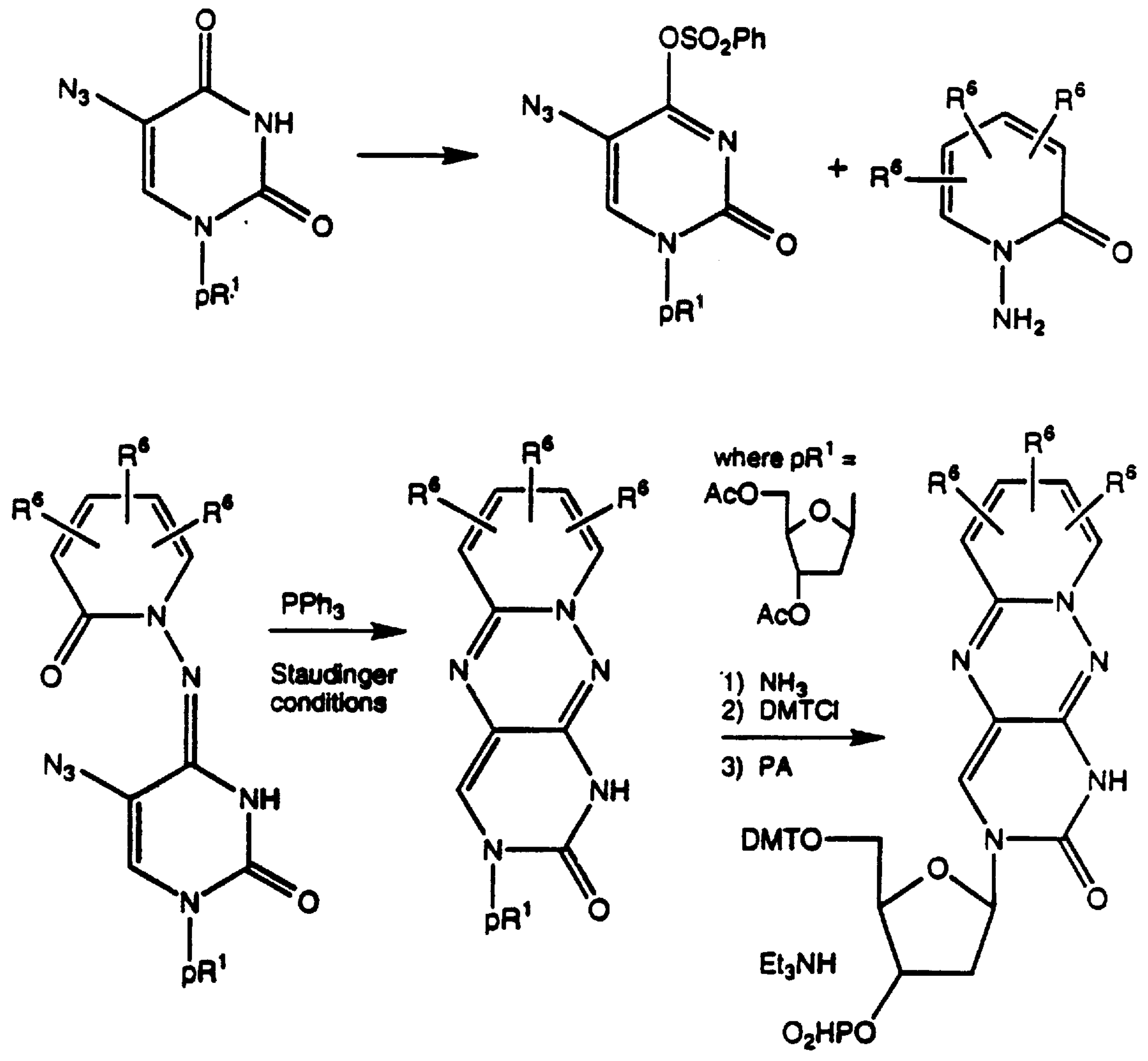
Figure 3:
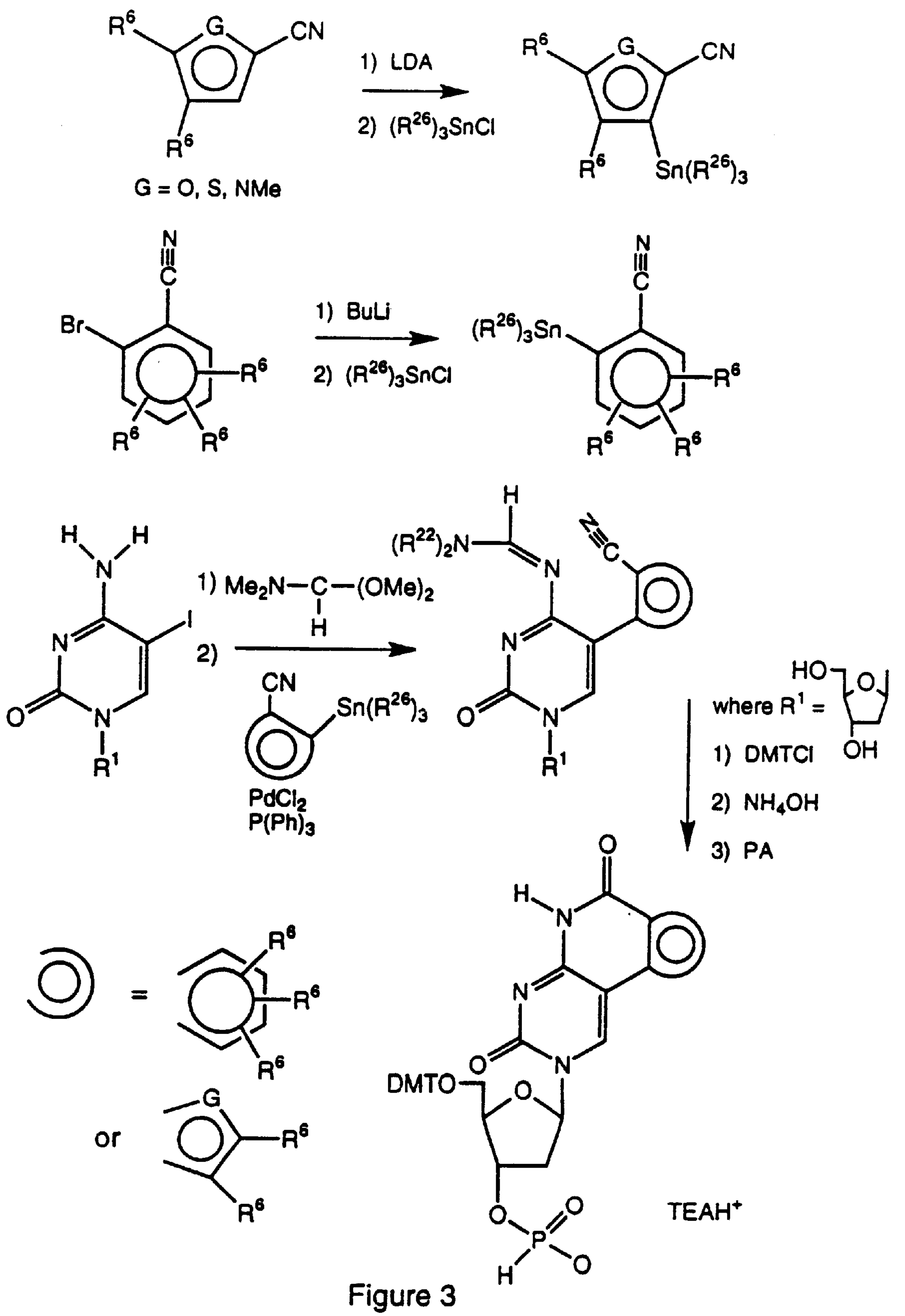
Figure 4:
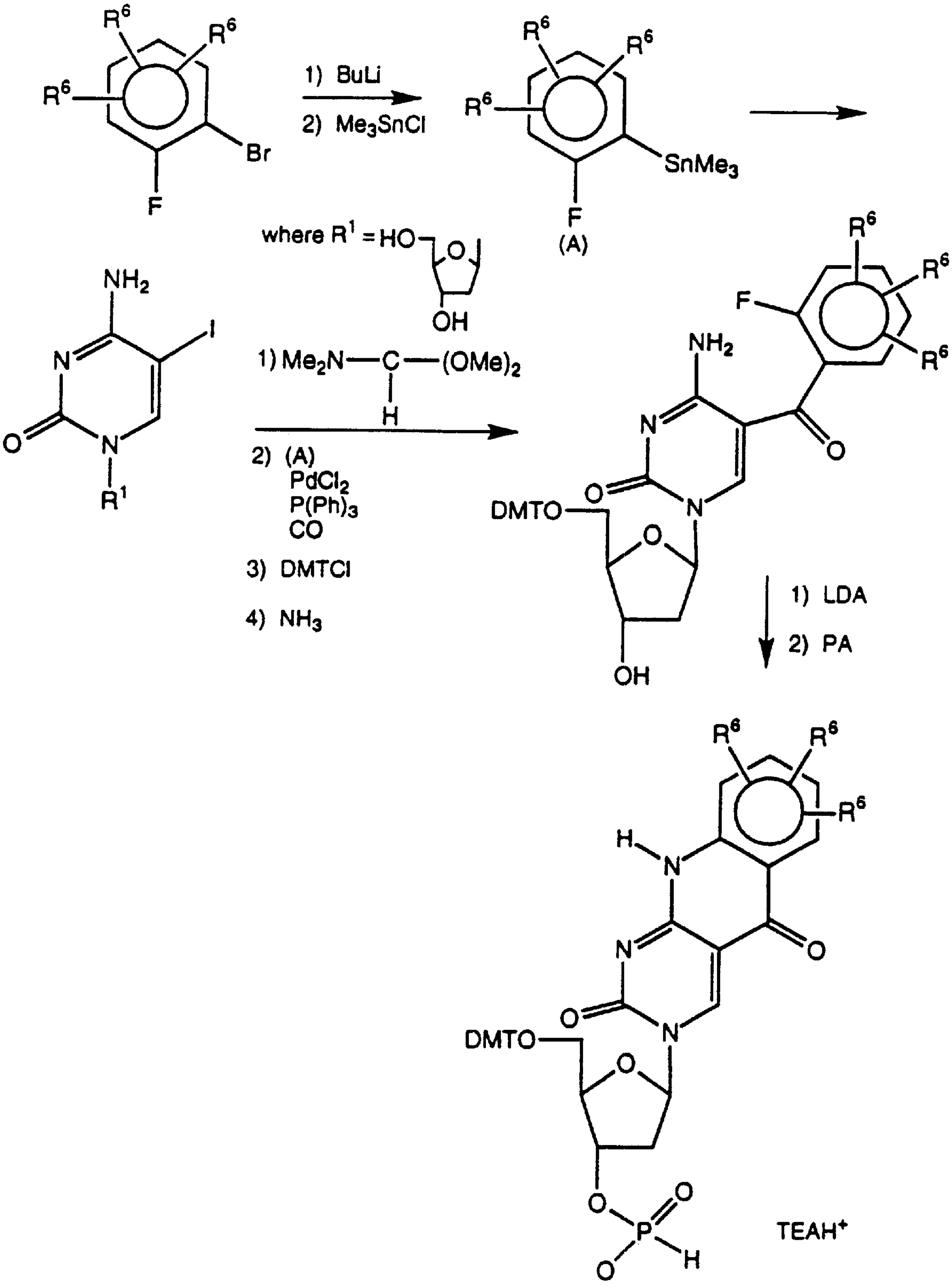

Compounds of structure (1) contain two interfunctional portions. The portion of structure (1) other than $R^1$ is refered to as the polycyclic substructure; it is fluorescent and participates in Watson-Crick base-pairing as well as stacking interactions. The remaining portion of the compounds of this invention, $R^1$, represents an H atom, a linking group or a binding partner The polycyclic substructure, the linking group and the binding partner are successively described below.

Compounds of Structure (1)—Polycyclic Substructure

The polycyclic substructure is a substantially planar fused heteroaryl or aryl functionality that generally serves as a cytosine surrogate for base-pairing and possesses the capability to participate in energy transfer either with other compounds having the polycyclic substructure or with fluorophores or chromogens which do not possess the polycyclic substructure. The polycyclic substructure base-pairs with guanosine, and in general will function as cytosine in hybridizing with nucleic acids or oligonucleotides. In addition, tautomers of the diazine substructure (9) below are capable of functioning as either cytosine analogues (where N* is protonated) or as thymine analogues (where $N^3$ is protonated).

(9)

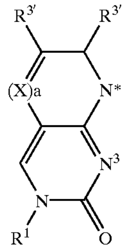

In structure (9), X, a and $R^1$ are defined above and both $R^{3'}$ groups are cyclized to complete a heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, 2 N ring heteroatoms separated by a carbon atom, or 3 N ring heteroatoms at least two of which are separated by a carbon atom, and wherein the aryl or heteroaryl ring carbon atoms are unsubstituted with other than H or at least 1 nonbridging ring carbon atom is substituted with $R^6$; and $R^6$ is defined above.

The polycyclic substructure consists of a pyrimidine radical fused to two or more fused heterocyclic or aryl rings. Typically, the ring structures fused to the pyrimidine radical comprise the following structures (10)–(17):

where (N) indicates the bond to pyrimidinyl N (10)

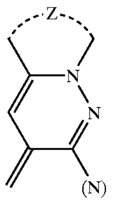

Diazine (11)

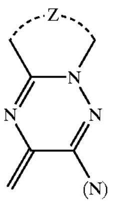

Triazine (12)

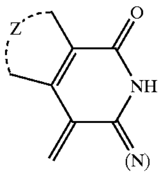

2-pyridone (13)

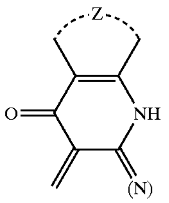

4-pyridone (14)

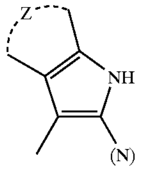

pyroline

-continued (15)

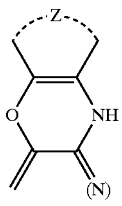

oxazine (16)

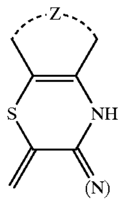

thiazine (17)

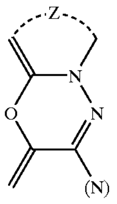

oxadiazine

The fused ring structure represented by Z is not critical. Typically Z, taken together with C—C or C—N of the adjacent ring, completes a single-ring aryl or heteroaryl radical containing 5 or 6 ring atoms, although in other embodiments $R^6$ groups on adjacent ring carbon atoms are taken together to complete an additional ring having 5 or 6 ring atoms, usually phenyl, thereby resulting in a fused bicycle. In those embodiments where Z is a heteroaryl radical, the heteroatoms are selected from the group consisting of 1–3 N atoms, 1 oxygen atom, 1 S atom, 1 oxygen and 1 N atom separated by at least 1 carbon atom, and 1 N atom and 1 S atom separated by at least 1 carbon atom. The Z ring structure is either unsubstituted with other than H or at least 1 nonbridging ring carbon atom is substituted with =O (or its tautomer) or $R^6$.

Ordinarily, Z is one of the following structures (18)–(20):

(18)

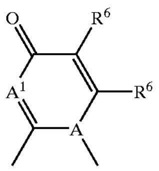

, (19)

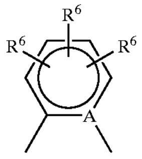

, or

-continued (20)

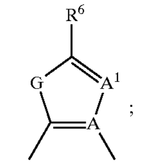

wherein $R^6$ is defined above;

$A^1$ is N or $CR^6$; and

G is CH, S, O or $NR^4$ where $R^4$ is defined below.

An embodiment of structure (19) is structure (21):

(21)

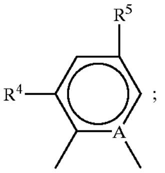

wherein $R^4$ is H or $C_1$–$C_6$ alkyl; and $R^5$ is H, $NO_2$ or $C_1$–$C_6$ alkyl.

An embodiment of structure (18) is structure (22):

(22)

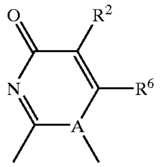

wherein $R^2$ is $C_1$–$C_6$ alkyl and $R^6$ is H.

Embodiments of structure (20) are structures (23)–(25):

(23)

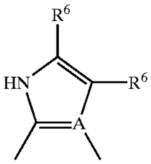

(24)

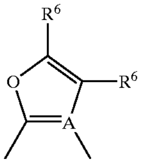

(25)

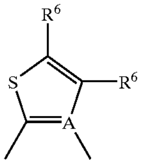

wherein A and $R^6$ are defined above.

Ordinarily, in the foregoing structures $R^6$ is H, $C_1$–$C_6$ alkyl (n, s or t), $NO_2$, $NH_2$, CN or halo, or adjacent $R^6$ are taken together to complete phenyl, although adjacent $R^6$ also are taken together to complete a thiazole, imidazole, oxazole, pyridine or pyrimidine ring. The $R^6$ amino groups are protected against electrophiles using a protecting group (typically base labile) when the polycyclic substructure is to be employed as an intermediate, particularly in those instances where $R^1$ is a linker intended for use in the preparation of an oligonucleotide.

Substituent $R^1$—Linkers $R^1$ linker groups are used to covalently bond the polycyclic substructure to the selected binding partner, although it will be understood that this need not be the sole utility for the linker functionality. Thus, a group present in $R^1$ linkers principally serves as the site for covalent bonding of the polycyclic substructure to a binding partner, typically by incorporation of the polycyclic substructure via the linker residue into a polymeric binding partner by grafting or copolymerization.

$R^1$ linkers also optionally are substituted with groups that ordinarily will not participate in binding to the binding partner, e.g., halo, azido and protected hydroxyl. Generally, the linker group will contain from 2 to about 50 atoms. If it contains a cycle the cyclic functionality typically will be an oxygen, sulfur or phosphorus-containing saturated or unsaturated heterocycle having a total of about from 5 to 7 ring atoms and 1 to 3 heteroatoms. For the most part the cycle will be a sugar, typically furanose or furanose substituted with phosphate, protected phosphate, hydroxyl or protected hydroxyl. Ordinarily, $R^1$ is an abasic nucleotide residue or such a residue derivatized so as to be capable of incorporation into an oligonucleotide. Thus, the $R^1$ linker frequently comprises an activated group or other group which can react with a polymer or other binding partner to be labeled with the polycyclic substructure. For example, groups described below that are compatible with commonly available oligonucleotide synthetic chemistries are useful. Other examples of reactant groups for covalent labeling are well-known from the diagnostic fields and have heretofore been used commonly to label proteins and oligonucleotide probes, as is more fully discussed below.

In one embodiment, $R^1$ is an organic linker group such as alkyl, alkene, alkyne, alkoxyalkyl, alkylthioalkyl, alkoxy, saturated or unsaturated heterocycle and the like which optionally is substituted with at least one group capable of being crosslinked with or incorporated into a polymer, e.g., such groups as hydroxy, amino, carboxyl, vinyl, phosphate or phosphonate. Typical examples of such linkers include $E—CHR^7—R^{11}—(CH_2)_{m1}—C(R^8)((CH^2)_{m1}(R^9))—(CH_2)_{m1}—R^{10}—(CH_2)_{m1}—$, $E—Q—C_6H_4—CH_2—$, $E—CHR^7—O—CHR^7—O—CHR^7—$, $E—CHR^7—(CHR^{13})—_{m1}—CHR^{14}—R^{10}—$, $H(CH_2)_{m1}CH(COOR^{20})(CH_2)_{m1}—$ (27)

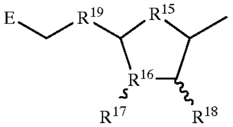

, (28)

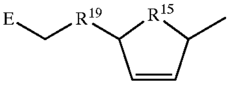

, and

-continued (29)

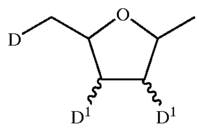

;

wherein

D is an oligonucleotide coupling group;

$D^1$ is independently F, H, O-alkyl, S-alkyl or an oligonucleotide coupling group, but only one $D^1$ is a coupling group;

Q is $—C(R^{12})_2—CH_2—$, $C(R^{12})_2—O—$, $—CR^{12}═CR^{12}—$, or $—C≡C—$;

$R^7$ is independently H or $C_1$–$C_4$ alkyl;

$R^8$ is H or $C_1$–$C_4$ alkyl, $C_2$–$C_4$ alkenyl or azidomethyl;

$R^9$ is halo, H or $OR^{20}$ $R^{10}$ is O, $CH_2$ or a covalent bond;

$R^{11}$ is O, S, $CH_2$, CHF or $CF_2$;

$R^{12}$ is independently H or halogen;

$R^{13}$ is H, halogen, $OR^{20}$, $CH_3$, $CH_2OR^{20}$ or $C_3$–$C_6$ acyloxyalkyl;

$R^{14}$ is H, halogen, $OR^{20}$, $CH_3$, $CH_2OR^{20}$, $C_3$–$C_6$ acyloxymethyl, or $C_2$–$C_6$ acyloxy, $R^{15}$ is $CH_2$, CHF or O;

$R^{16}$ is CH or S, provided that when $R^{19}$ is 0 or S, or $R^{15}$ is CH, then $R^{16}$ is not S;

$R^{17}$ is H, $OR^{20}$, halogen, $N_3$, $C_1$–$C_4$ alkyl or $C_1$–$C_4$ alkoxy or is absent when $R^{16}$ is S;

$R^{18}$ is H, $OR^{20}$, halogen, $N_3$, $C_1$–$C_4$ alkyl or $C_1$–$C_4$ alkoxy;

$R^{19}$ is O, S, $CH_2$, CHF or $CF_2$;

$R^{20}$ is H or a protecting group;

m1 is independently 0 or an integer from 1 to 4; and

E is OH, $OR^{20}$, $—PO_2$ or $—OP(O)_2$.

In some embodiments of this invention the linker group is $HOCH(CHR^{13})CH_2—$ or $ECH_2OCH(CHR^{13})CH_2—$. In embodiments of the invention where the compound of structure (1) is to be used as a monomer in the preparation of oligonucleotides, $R^1$ is substructure (29) above in which D or $D^1$ are oligonucleotide coupling groups. "Coupling group" as used herein means any group suitable for generating a linkage or phosphodiester substitute linkage between nucleotide bases or their analogues. These coupling groups are conventional and well-known for the preparation of oligonucleotides, and are prepared and used in the same fashion here. They may be configured as the beta anomers as denoted in substructure (29) or as the alpha anomers. In general, each compound comprising substructure (29) will contain two coupling groups: D or $D^1$, but with only one $D^1$ being a coupling group. The coupling groups are used as intermediates in the preparation of 3'-5' 5'-3', 5'-2' and 2'-5' internucleotide linkages in accord with known methods.

Figure 12A:
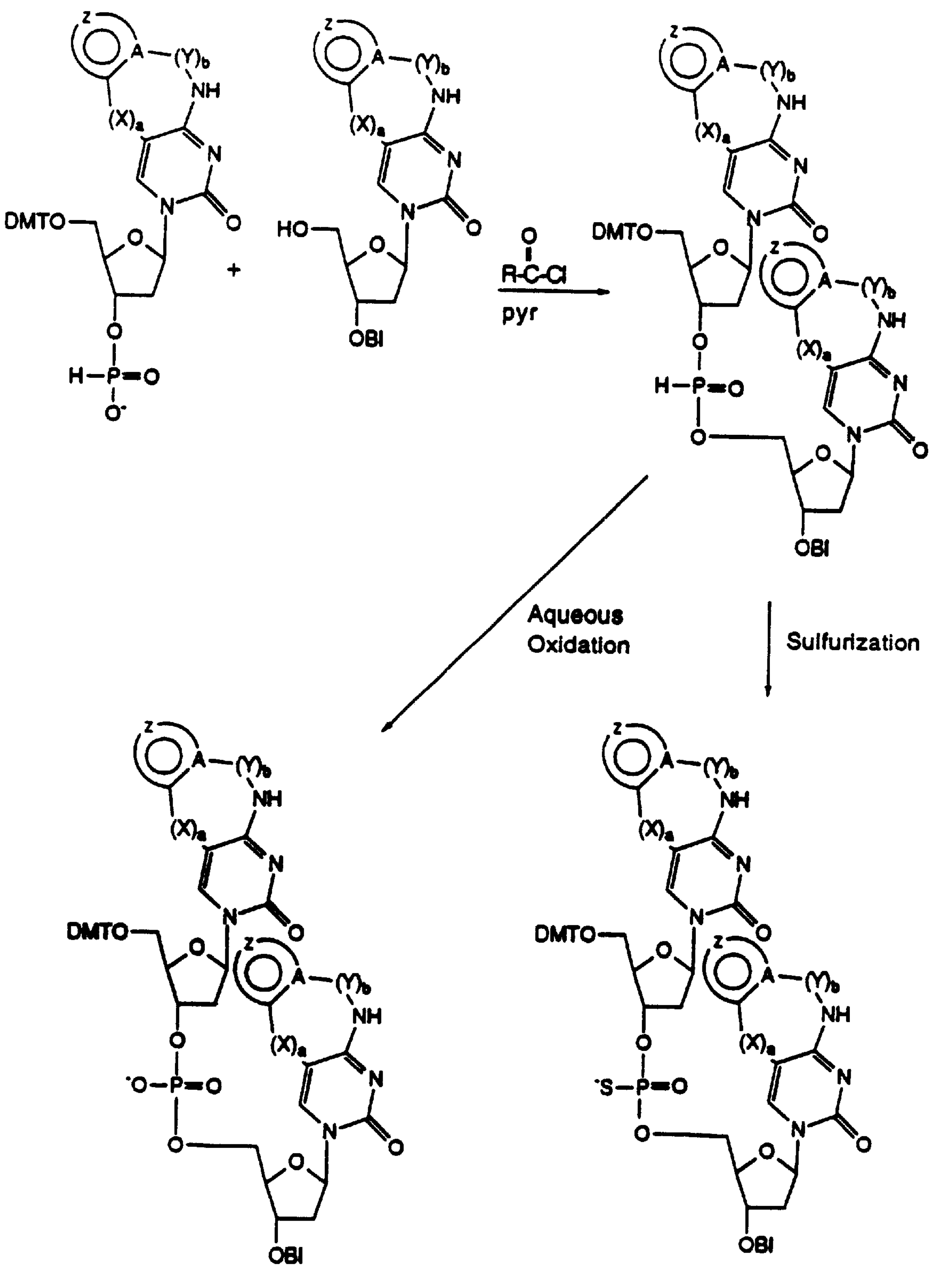
FIGS. 12A–12C depict synthetic methods for the preparation of oligomers of this invention containing derivatized phosphodiester linkages.

Suitable coupling groups for phosphodiester linkages include OH, H-phosphonate (FIG. 12A); (for amidite chemistries) alkylphosphonamidites or phosphoramidites such as beta-cyanoethylphosphoramidite (FIG. 12-B and 12-C), N, N-diisopropylamino-beta-cyanoethoxyphosphine, N,N-diisopropylamino-methoxyphosphine, N,N-diethylamino-methoxyphosphine, N,N-diethylamino-beta-cyanoethoxyphosphine, N-morpholino-beta-cyanoethoxyphosphine, N-morpholino methoxyphosphine, bis-morpholino-phosphine, N,N-dimethylamino-beta-cyanoethylmercapto-phosphine, N,N dimethylamino-2,4-dichlorobenzylmercapto-phosphine, and bis(N,N-diisopropylamino)-phosphine; and (for triester chemistries) 2-, or 4-chlorophenyl phosphate, 2,4-dichlorophenyl phosphate, or 2,4-dibromophenyl phosphate. See for example U.S. Pat. Nos. 4,725,677; 4,415,732; 4,458,066; and 4,959,463; and PCT 92/07864. If $D^1$ is a coupling group then D typically will be hydroxyl blocked with a group suitable for ensuring that the monomer is added to the oligomer rather than dimerizing. Such groups are well known and include DMT, MMT, FMOC (9-fluorenylmethoxycarbonyl), PAC (phenoxyacetyl), a silyl ether such as TBDMS (t-butyldiphenylsilyl) and TMS (trimethylsilyl). Obviously, the opposite will apply when one desires to synthesize an oligomer in the opposite direction (5'→3'). Ordinarily, D is DMT, $D^1$ is located on the 3' carbon, the remaining $D^1$ is H and the $D^1$ groups are in the alpha anomer conformation.

Substituent $R^1$—Binding Partner

A binding partner is any substance that is desired to be detected (analyte) or a substance that non-covalently binds to the analyte. Binding partners are well-known from the immunoassay art and include hapten-antibody pairs such as those exploited in drug immunoassays using EMIT or ELISA technologies. Binding partners are employed analytically in enzymology, where the substrate or the enzyme is labeled. Binding partners also are known from the oligonucleotide hybridization art, including oligonucleotide-nucleic acid binding partners (as in diagnostic probes or therapeutic antisense oligonucleotides) or oligonucleotide-protein binding partners (aptamers). In accordance with this invention, the polycyclic substructure is substituted at $R^1$ by any binding partner. While the binding partner may be a small molecule such as a drug, hapten, substrate or the like, ordinarily it is a polymer.

Compounds of structure (1) wherein $R^1$ is a polymer are an important feature of this invention. For the most part, when $R^1$ is a polymer an $R^1$ linker group has been subsumed into the polymer structure, either as a monomer unit or by grafting onto preexisting polymer. Therefore, when $R^1$ is a polymer it will be understood that the polymer may comprise the residue of a linking group wherein the linker residue originated with a monomeric subunit or was extraneous to the monomeric subunits of the polymer. All that is needed is that the polycyclic substructure be covalently bound to the polymer.

The nature of the polymer is not critical Typically $R^1$ polymers include a biopolymer such as an oligonucleotide, protein (including antibodies, enzymes, cell membrane proteins, glycoproteins, glycolipids, lipoproteins and nucleoproteins), peptide, nucleic acid, or glycan or other polysaccharide or carbohydrate. In certain embodiments the polymer is an oligonucleotide analogue in which either or both of the sugar or phosphodiester subunits have been substituted by groups that continue to permit base pairing by the polycyclic substructure but which have other desirable characteristics which are not shared with native substituents, e.g., those which mask the negative charges of the phosphodiester linkages or replace the phosphodiester linkage with another group.

The site of polymer substitution by the structure (1) polycycle is not critical. In general, any reactive group on the polymer is satisfactory when it is desired to graft the linker-substituted polycyclic substructure onto a preexisting polymer. Obviously, the site of the substitution should not be in a location in which the polycyclic substructure will interfere with the intended function for the polymer, e.g. enzyme active site, antibody CDR, and the like as will be understood by the artisan. An amino acid side chain such as that of lysine, glutamic acid, serine, asparagine and the like will be satisfactory for grafting to protein $R^1$, as will alpha amino groups, provided that the amino acids in question do not participate in the binding partner or ligand/substrate interaction involved in the assay in which the labeled protein is to be used. The same reasoning is used to select a binding site or sites on other analytes such as sugars, glycans, lipids, and the like. For example, the 1' position of ribose or deoxyribose is satisfactory as the site of substitution of an oligonucleotide by the polycyclic substructure. Suitable sites will be known to the artisan, particularly in those instances where the polycyclic substructure is intended to substitute for other fluorescent labels heretofore employed.

The degree of substitution by the polycyclic base of this invention is not critical. One skilled in the art will choose the reaction conditions such that the resulting labeled polymer will be substituted with sufficient molar proportion of polycyclic substructure to facilitate its use in the desired analytical, therapeutic or preparative procedure. This is accomplished by preparing the labeled polymers under a variety of heretofore conventional conditions, e.g., the time, temperature or duration of the labeling reaction, to yield a matrix of multiply-labeled polymers. These then are screened for suitability in the intended application. Molar ratios of about from 1:1 to 10:1 label to polymer generally are suitable. Where the labeled polymer is prepared by monomer incorporation, the resulting polymer may contain about from 1% to 100% polycyclic substructure substitution. In this embodiment each polycyclic base of this invention is considered a monomer unit (even though the polymer may have been assembled from intermediate synthons containing 2 or more inventive polycyclic substructures per synthon).

Oligomers are polymers containing at least 2 nucleotides or nucleotide analogues, at least one of which comprises a polycyclic substructure of this invention. In most embodiments of this invention at least one polycyclic substructure is covalently linked to a nucleotide base, or to the same or a different polycyclic substructure, by an organic moiety that is sufficiently flexible to permit the bases and substructure(s) to hybridize to complementary bases. This linkage may be a conventional phosphodiester linkage in which a nucleotide analogue containing the polycyclic substructure (where $R^1$ is deoxyribosyl or ribosyl) is incorporated into an oligonucleotide by conventional methods. Alternatively, other groups are used to replace the phosphodiester linkage or, in some instances,. both of the phosphodiester linkage and the sugar group. These replacement groups are termed substitute linkages for the purposes herein.

Figure 12B:
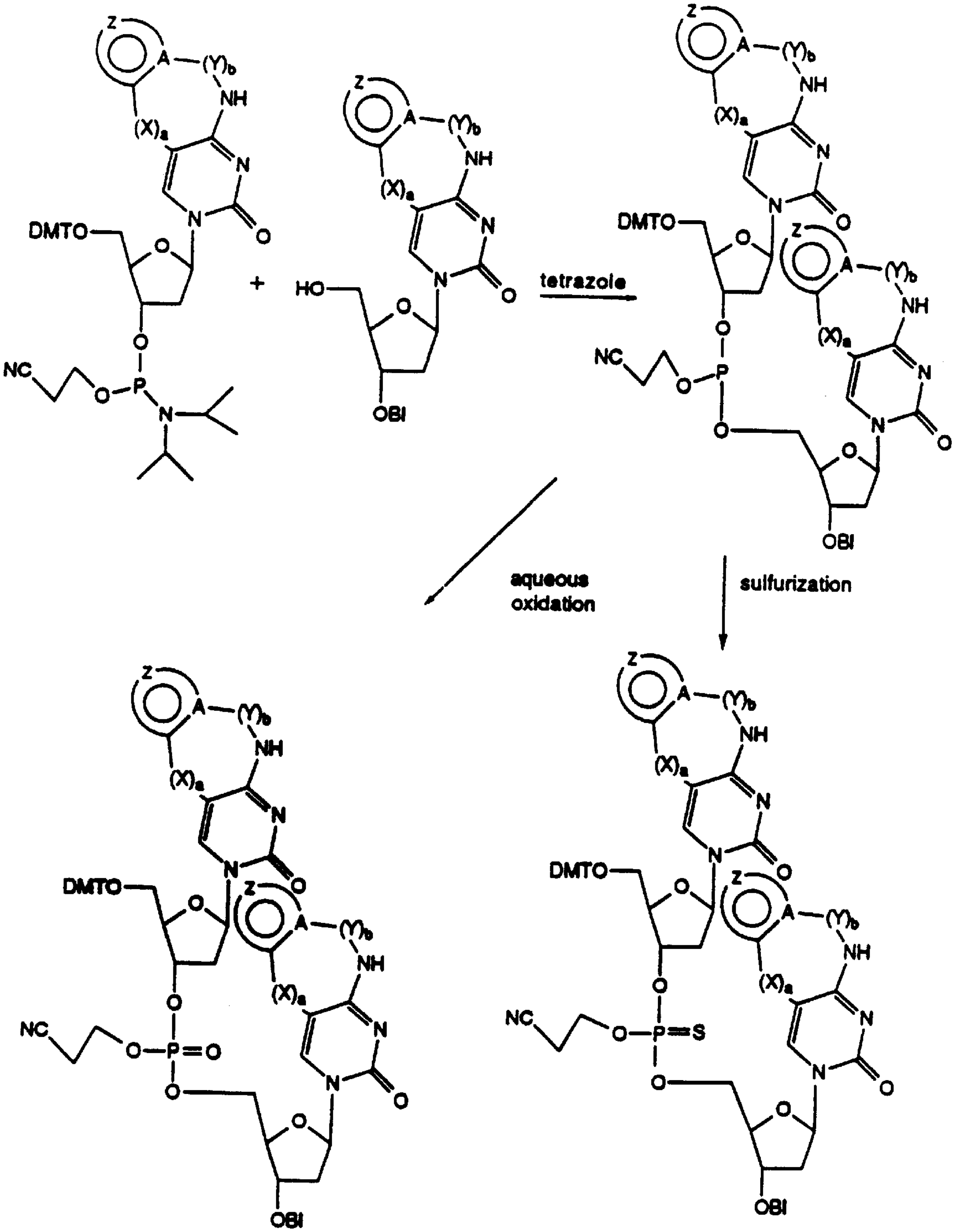
Figure 12C:
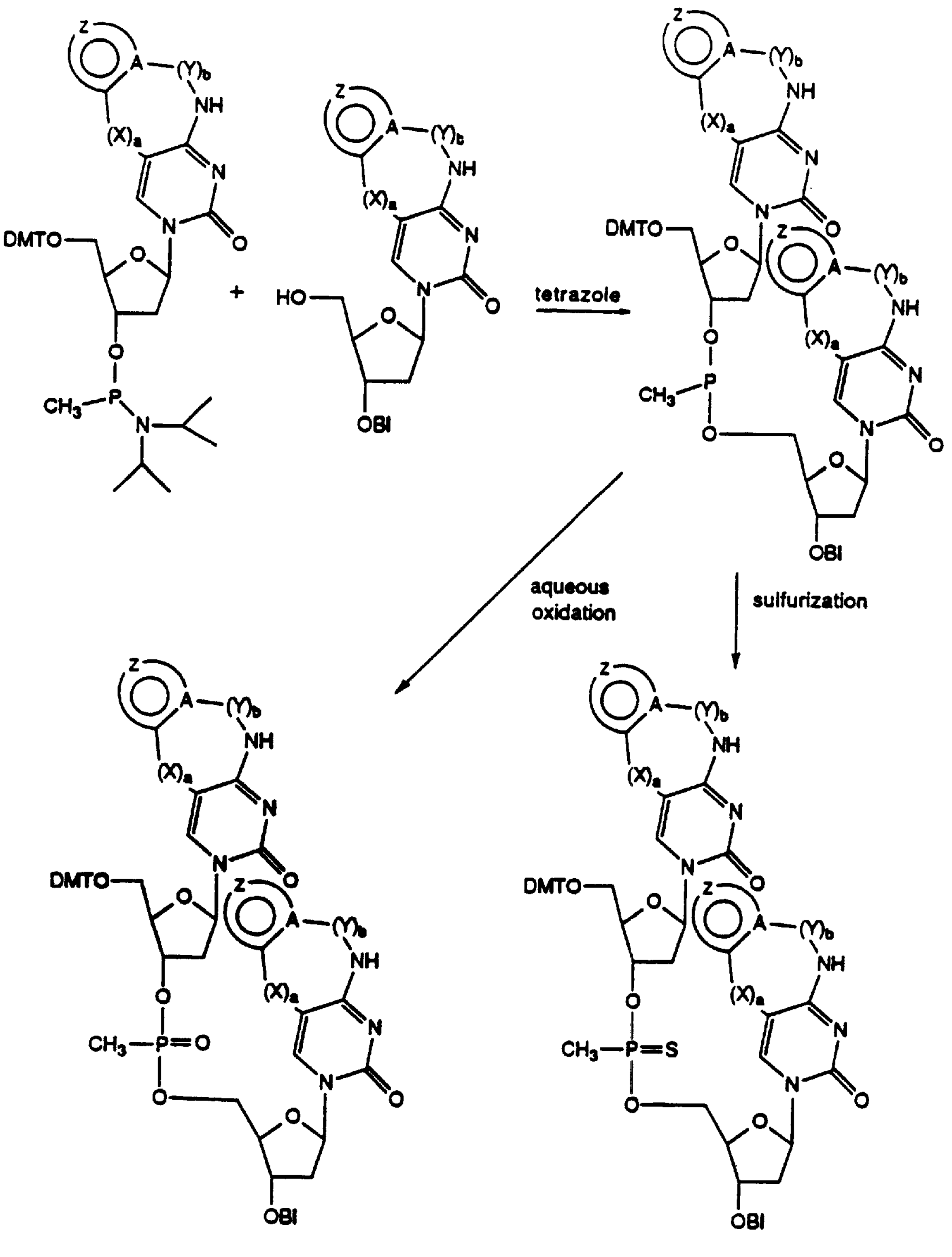

Substitute linkages are well-known from the prior literature. They include for example phosphorodithioates (Marshal, "Science" 259:1564, 1993), phosphorothioates and alkylphosphonates (Kibler-Herzog, "Nucleic Acids Research" [hereafter "NAR"] 19:2979, 1991; PCT 92/01020; EP 288,163; FIG. 12-1), phosphoroamidates (Froehler, "NAR" 16:4831, 1988), phosphotriesters (Marcus-Sekura, "NAR" 15:5749, 1987), boranophosphates (Sood, "J. Am. Chem. Soc." [hereafter JACS] 112:9000, 1991), 3'-O-5'-S-phosphorothioates (Mag, "NAR" 19:1437, 1991), 3'-S-5'-O-phosphorothioates (Kyle, "Biochemistry" 31:3012, 1992), 3'-$CH_2$-5'-phosphonates (Heinemann, "NAR" 19:427, 1991), 3'-NH-5'-O-phosphonates (Mag, "Tet. Ltt." 33:7323, 1992), sulfonates and sulfonamides (Reynolds, "J. Org. Chem." [hereafter "JOC"] 57:2983, 1992), sulfones (Huie, "JOC" 57:4519, 1992), sulfoxides (Huang, "JOC" 56:3869, 1991), sulfides (Schneider, "Tet Ltt." 30:335, 1989), sulfamates, ketals and formacetals (Matteucci, "JACS" 113:7767, 1991, PCT 92/03385 and PCT 90/06110), 3'-thioformacetals (Jones, "JOC" 58:2983, 1993), 5'-S-thioethers (Kawai, "Nucleosides Nucleotides" 10:1485, 1991), carbonates (Gait, "J. Chem. Soc. Perkin Trans 1" 1389, 1979), carbamates (Stirchak "JOC" 52:4202, 1987), hydroxylamines (Vasseur, "JACS" 114:4006, 1992), methylamine (methylimines) and methyleneoxy (methylimino) (Debart, "Bioorg. Med. Chem. Lett." 2:1479, 1992) and amino (PCT 91/06855). Also of interest are hydrazino and siloxane (U.S. Pat. No. 5,214,134) linkages.

Substitute linkages per se also are known for the replacement of the entire phosphoribosyl linkage of conventional oligonucleotides. These include for example morpholino-carbamates (Stirchak, "NAR" 17:6129, 1989), peptides (Nielsen et al., "Science" 254:1497, 1991; U.S. Ser. Nos. 07/892,902 and 07/894,397), and riboacetal linkages (PCT 92/10793).

Additional disclosure of substitute linkages is found in PCT 91/08213, 90/15065, 91/15500, 92/20702, 92/20822, 92/20823, 92/04294, 89/12060 and 91/03680; Mertes, "J. Med. Chem." 12:154, 1969; Mungall, "JOC" 42:703, 1977; Wang, "Tet Lett" 32:7385, 1991; Stirchak, "NAR" 17:6129, 1989; Hewitt, "Nucleosides and Nucleotides" 11:1661, 1992; and U.S. Pat. Nos. 5,034,506 and 5,142,047.

The phosphodiester or substitute linkages herein are used to bond the 2' or 3' carbon atoms of ribose or ribose analogues to the 5' carbon atoms of the adjacent ribose or ribose analogue. Ordinarily, the linkages in oligonucleotides are used to bond the 3' atom of the 5' terminal oligonucleotide to the 5' carbon atom of the next 3'-adjacent nucleotide or its analogue.

Table 1 below sets forth various examples of suitable substitute linkages for use with the polycyclic nucleotide analogue bases of this invention. The columns designated D (5') and $D^1$ (3' or 2') describe the substructure (29) substituents used to produce the $X^1$ linkage of structure (8), shown in the right column, using methods known per se in the art and described in U.S. Ser. No. 07/892,902 and other citations above. The starting materials in Table 1, or those used to prepare the starting materials of Table 1, generally possess structure (1) in which $R^1$ is ribose or a ribose analogue comprising a 5' hydroxyl group and a 3' or 2' hydroxyl group, prepared as described herein or in the citations, with the polycyclic base being substituted for the bases used in the citations. Sequentially useful starting materials are designated by an arrow. Bracketed monomers are reacted to form dinucleotide analogues having the $X^1$ substitute linkage. The reactions are repeated or ganged with phosphodiester linkages in order to produce trimers, tetramers or larger oligomers, including up to about 98 bases.

B1 means a blocking group. As used herein, "blocking group" refers to a substituent other than H that is conventionally attached to oligomers or nucleotide monomers, either as a protecting group, a coupling group for synthesis, $PO_3^{-2}$, or other conventional conjugate such as a solid support. As used herein, "blocking group" is not intended to be construed solely as a nucleotide protecting group, but also includes, for example, coupling groups such as hydrogen phosphonate, phosphoramidite and others as set forth above. Accordingly, blocking groups are species of the genus of "protecting groups" which as used herein means any group capable of preventing the O-atom or N-atom to which it is attached from participating in a reaction involving an intermediate compound of structure (1) or otherwise forming an undesired covalent bond. Such protecting groups for O- and N-atoms in nucleotide monomers or nucleoside monomers are described and methods for their introduction are conventionally known in the art. Protecting groups also are useful to prevent reactions and bonding at carboxylic acids, thiols and the like as will be appreciated by those skilled in the art.

TABLE 1

Substitute Linkages

| D (5') | $D^1$-(3' or 2') | 2'/3'-$X^1$-5' |
|---|---|---|
| $OH \rightarrow DMTO$ | $—CH_2CH{=}CH_2 \rightarrow CH_2CHO$ | $—(CH_2)_2—NHCH_2—$ |
| $NH_2$ | OBl | |
| $OH \rightarrow DMTO$ | $N_3 \rightarrow NH_2$ | $—NH(CH_2)_2—$ |
| $CH_2C(OEt)_2$ | —OBl | |
| $OH \rightarrow DMTO$ | $—CH_2CH{=}CH_2 \rightarrow CH_2CHO—$ | $—CH_2NH(CH_2)_2—$ |
| $—CH_2NH_2$ | —OBl | |
| $OH \rightarrow DMTO$ | $OH \rightarrow —OCH_2CH{=}CH_2$ | $—O(CH_2)_2NHCH_2—$ |
| $—CH_2NH_2$ | —OBl | |
| $OH \rightarrow —CH_2CH{=}CH_2$ | OBl | $—NH(CH_2)_2OCH_2—$ |
| $OH \rightarrow DMTO$ | $NH_2$ | |
| DMTO | CHO | $—CH_2NHCH_2—$ |
| $—NH_2$ | OBl | |
| $CH_2CN \rightarrow CH_2CHO$ | OBl | $—NH(CH_2)_2—$ |
| DMTO | $NH_2$ | |
| $(CH_2)_2OH \rightarrow (CH_2)_2OTs$ | OBl | $—S(CH_2)_3—$; $—S(O)(CH_2)_3—$; or $—S(O)(O)(CH_2)_3—$ |
| DMTO | SH | |
| $CH_2OH \rightarrow CH_2Br$ | OBl | $—S(CH_2)_2—$; $—S(O)(CH_2)_2—$; or $—S(O)(O)(CH_2)_2—$ |
| DMTO | SH | |
| DMTO | $CH_2O \rightarrow CH_2OH \rightarrow CH_2OTS$ | $—CH_2SCH_2—$; $—CH_2S(O)CH_2—$; or $—CH_2S(O)(O)CH_2—$ |
| SH | OBl | |
| $TsOCH_2$ | OBl | $—O(CH_2)_2—$ |
| DMTO | OH | |
| DMTO | $CH_2CHO \rightarrow CHO \rightarrow (CH_2)_2OH$ | $—(CH_2)_2OCH_2—$ |
| $OH \rightarrow MsO$ | OBl | |
| DMTO | NHalk(C1-6) | $—N(alk)(CH_2)_3—$ |
| $CH_2CHO$ | OBl | |
| DMTO | $NH(COOEt) \rightarrow N(COOEt)(CH_2SCH_3)$ | $—N(COOEt)CH_2OCH_2—$ |
| OH | OBl | |
| $(CH_2)_2I$ | OBl | $—S(CH_2)_3—$ |
| DMTO | SH | |
| TolO | $NH_2$ | $—NHC(O)OCH_2—$ |
| pNPhOC(O)O | OBl | |
| TolO | $OCH_2Cl$ | $—OCH_2SCH_2—$ |
| SH | OBl | |
| TolO | OC(O)OpNPh | $—OC(O)N(R)CH_2—$ |
| —NHR | OBl | |
| TolO | $OCH_2SMe$ | $—OCH_2OCH_2—$ |
| OH | OBl | |
| DMTO | SH | $—SCH_2OCH_2—$ |
| $OCH_2Cl$ | OBl | |
| DMTO | OH | $—OCH_2CH{=}CH—$ |
| $BrCH_2CH{=}$ | —OBl | |
| DMTO | SH | $—SCH_2CH{=}CH—$ |
| $BrCH_2CH{=}$ | —OBl | |

(R = H or lower alkyl)

The oligomers of this invention contain naturally occuring nucleotides or derivatives thereof. In some oligonucleotide embodiments the companion nucleotide residues contain pyrimidine nucleotides substituted at the 5 position with a carbon atom which is distally Pi bonded to another atom as for instance 1-alkenyl, 1-alkynyl, heteroaromatic and 1-alkynyl-heteroaromatic groups such as 5-propynyl-cytosine and -uridine nucleotides (see US 92/10115 and U.S. Ser. No. 08/050,698). Other analogs of native bases for use herein include alkylated purines or pyrimidines, acylated purines or pyrimidines, or other analogues of purine or pyrimidine bases and their aza and deaza analogues. These include, for example $N^4$,$N^4$-ethanocytosine, 7-deazaxanthosine, 7-deazaguanosine, 8-oxo-$N^6$-methyladenine, 4acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, inosine, $N^6$-isopentenyl-adenine, 1-methyladenine, 2-methylguanine, 5-methylcytosine, $N^6$-methyladenine, 7-methylguanine, 5-methylaminomethyl uracil, 5-methoxy aminomethyl-2-thiouracil, 5-methoxyuracil, pseudouracil, 5-methyl-2-thiouracil, 2-thiouracil, 4thiouracil, 5-(1-propynyl)4thiouracil, 5-(1-propynyl)-2-thiouracil, 5-(1-propynyl)-2-thiocytosine, 2-thiothymidine, and 2,6-diaminopurine. In addition to these base analogs, pyrimidine analogs including 6-azacytosine, 6-azathymidine and 5-trifluoromethyluracil described in Cook, D. P., et al, International Publication No. WO 92/02258 can be conveniently incorporated into the invention oligomers.

Preferred bases include adenine, guanine, thymine, uracil, cytosine, 5-methylcytosine, 5-(1-propynyl)uracil, 5-(1-propynyl)cytosine, 8-oxo-$N^6$-methyladenine, 7-deaza-7-methylguanine, 7-deaza-7-methyladenine and 7-deazaxanthosine.

Embodiments of the oligomers of the invention comprise a moiety which is capable of effecting at least one covalent bond between the oligomer and a nucleic acid duplex or strand. Multiple covalent bonds can also be formed by providing a multiplicity of such crosslinking moieties. The covalent bond is preferably to a base residue in the target strand, but can also be made with other portions of the target, including the saccharide or phosphodiester. Preferred crosslinking moieties include acylating and alkylating agents, and, in particular, those positioned relative to the sequence specificity-conferring portion so as to permit reaction with the target location in the strand. Exemplary crosslinking moieties are disclosed and claimed in PCT 91/03680. See also Praseuth ("P.N.A.S. USA" 85:1349, 1988), Fedorova ("FEBS" 228:273, 1988), Meyer ("J. Am. Chem. Soc" 111:8517, 1989), Lee ("Biochemistry" 27:3197, 1988), Horne ("J. Am. Chem. Soc." 112:2435, 1990), Shaw ("J. Am. Chem. Soc." 113:7765, 1991).

Oligomers of inverted polarity also fall within the scope of this invention. "Inverted polarity" means that the oligomer contains tandem sequences which have opposite polarity, i.e., one having polarity 5'→3' followed by another with polarity 3'→5', or vice versa. These sequences thus are joined by linkages which can be thought of as effectively a 3'-3' internucleoside junction (however the linkage is accomplished), or effectively a 5'-5' internucleoside junction. For a further description of suitable methods for making such oligomers see PCT 92/10115. Compositions of "parallel-stranded DNA" designed to form hairpins secured with AT linkages using either a 3'—3' inversion or a 5'—5' inversion have been synthesized by van de Sande ("Science" 241:551, 1988). In addition, oligomers which contain 3'—3' linkages have been described (Horne, op cit; and Froehler "Biochemistry" 31:1603, 1992). These oligomers are useful as binding partners for double stranded nucleic acids to form triple helix (or triplex) complexes as a means for inhibition of the expression of target gene expression (PCT 89/05769 and 91/09321).

Methods for Synthesis

The compounds of structure (1) where $R^1$ is a linker or H are prepared by methods known in the art per se and as more fully described below. Typically, such compounds are prepared from cytosine or cytosin-1-yl linker substituted derivatives as shown in the synthetic schemes of FIGS. 1–10, whereby the starting material is already substituted with $R^1$ and the subsequent reactions are directed to closing the polycyclic ring. In these embodiments the hydroxyl, amino and any other labile groups of $R^1$ are protected as required by the schemes. In another approach, $R^1$ of the starting material is H and the linker is added after the ring closure steps set forth in the schemes, in the same fashion as has heretofore been employed in the alkylation of pyrimidine bases intended for use as antiviral compounds. For example, conventional procedures exist for alkylating pyrimidine bases with an appropriate organophosphorus synthon having a preformed $R^1$ substructure. These chemistries are well-known previously for the preparation of acyclic and cyclic nucleosides, nucleotides and nucleotide phosphonate analogues. They are readily adapted for use with the schemes described herein for preparation of compounds of structure (1) wherein $R^1$ is a linker or H.

Figure 5:
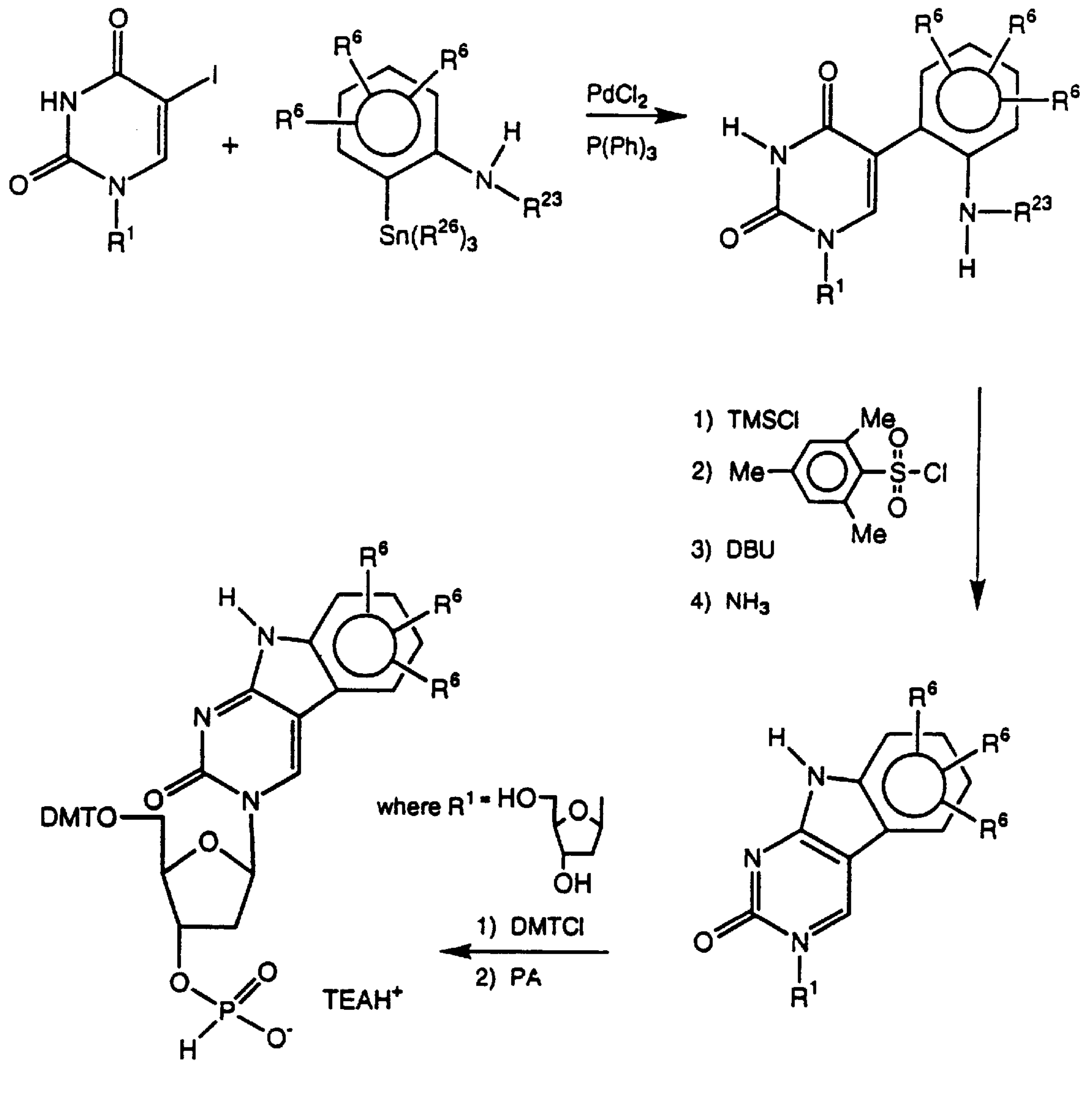
Figure 6:
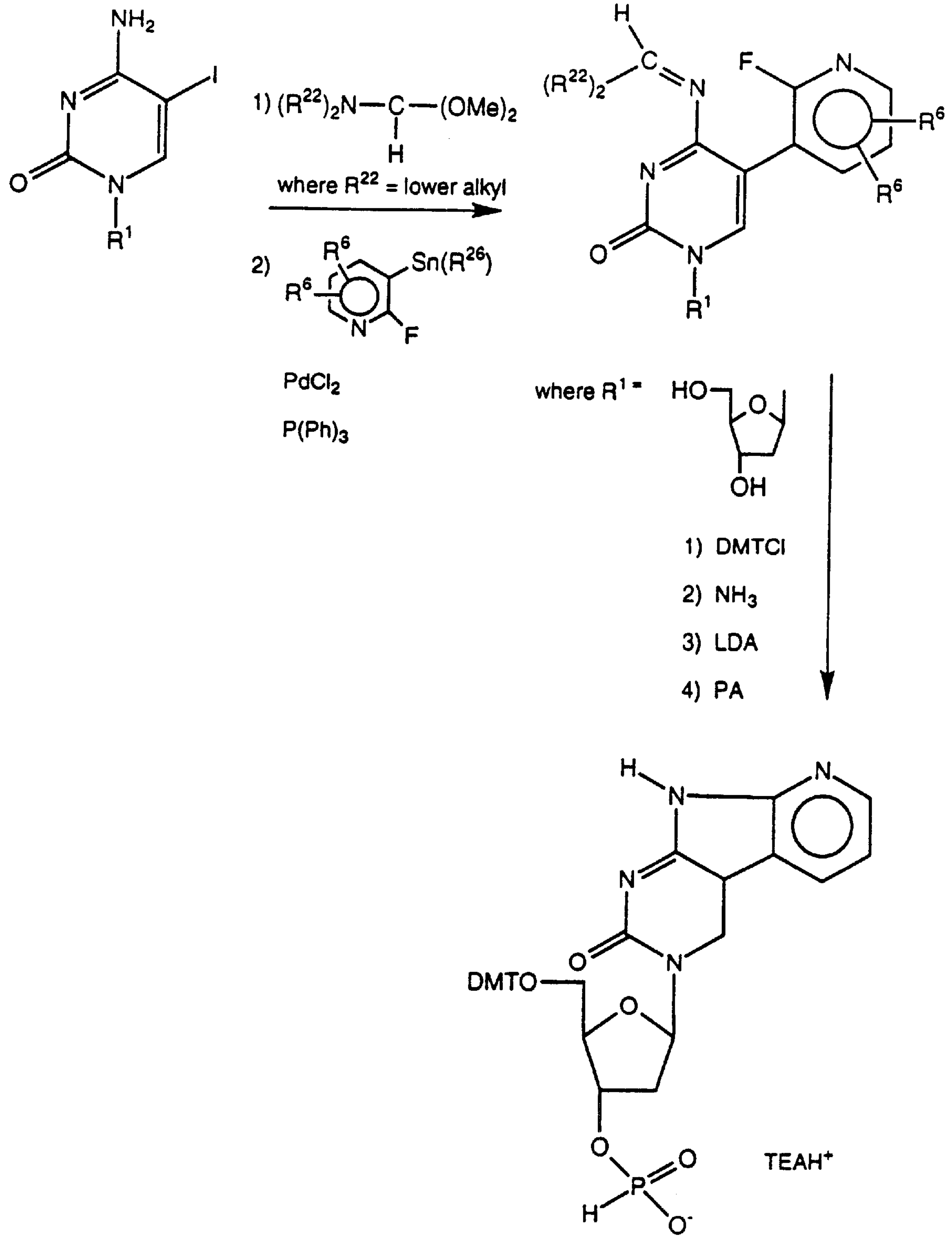

The scheme of FIG. 6 is preferred for fused pyrroline compounds in which the ring immediately fused to the pyrimidinyl radical is an N-containing heterocycle; if this ring is aryl, the FIG. 5 scheme is preferred.

Figure 11:
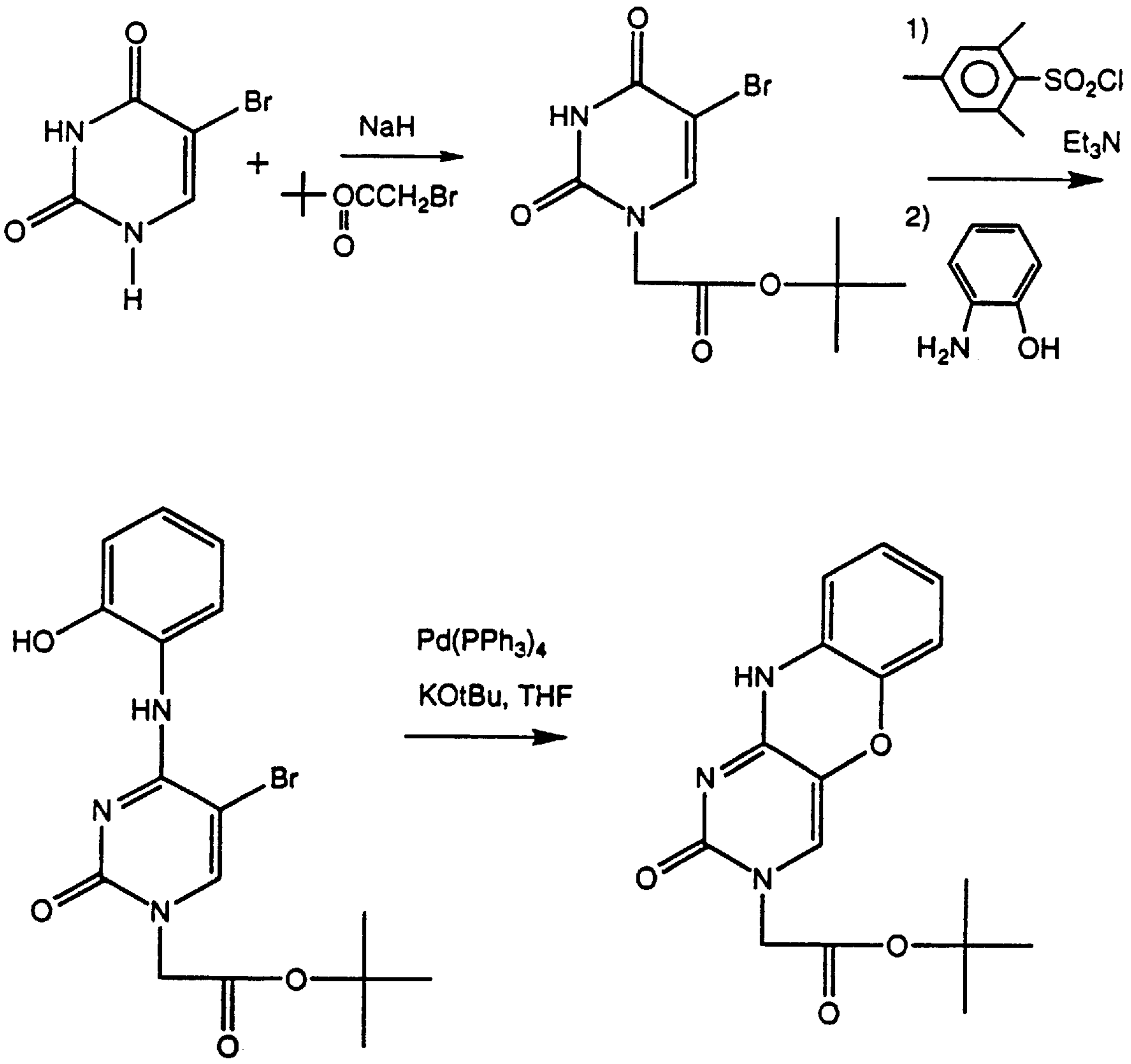
FIG. 11 depicts a scheme for the preparation of a linker-substituted thiazine derivative.

The scheme of FIG. 11 is useful in preparing starting materials for peptide substitute linkages of the sort disclosed in Nielsen et al, op cit., or for preparing carboxyalkyl linkers for cross-linking to, or incorporation into, proteins or polypeptides.

In those embodiments in which $R^1$ is a binding partner such as a polymer the compounds of this invention are synthesized by covalently crosslinking the linker modified polycyclic base of this invention to the binding partner, or (where the binding partner is a polymer) by incorporating into the polymer a monomer unit which is substituted by the polycyclic base of this invention.

In the first embodiment (polymer grafting) a linker-substituted polycyclic substructure is covalently bonded via any conventional cross-linking agent to the polymer. Most conveniently, structure (1) compounds in which $R^1$ is hydroxyl- or amino-substituted alkyl are readily cross-linked to reactive groups present in the molecule to be labeled as noted above. Typical cross-linking agents include succinic anhydride, DCC, EDC, BOP, and glutaraldehyde. Cyanogen bromide activated carbohydrates also are used. The cross-linking agents are used to bond the linker-substituted polycycle to the polymer in the same fashion as polymers heretofore have been cross-linked to ligands, e.g., to hydroxyl or amino-bearing moieties. An example of a suitable method is described per se in Cook et al., U.S. Pat. No. 5,218,105. This method is readily applied to covalently bond an amino-substituted $R^1$ linker to the 5' terminus of an oligonucleotide.

In the second embodiment (copolymerization) the linker is capable of functioning as a monomer for copolymerization with other monomer units that may or may not be substituted with the polycyclic substructure of structure (1). In some embodiments, the $R^1$ linker is an alkyl carboxylate, an alkyl amine or an amino acid for incorporation into peptides by in vitro methods. However, in the typical embodiment the $R^1$ polymeric binding partner is an oligonucleotide as depicted in structure (8), and these conveniently are made by copolymerization with a nucleotide analogue substituted with the polycycic substructure. The starting materials for the synthesis of structure (8) generally are compounds of structure (1) in which $R^1$ is ribose or deoxyribose substituted with appropriate blocking and coupling groups further described above. Suitable starting monomers for oligonucleotides having substitute linkages are set forth in Table 1, and they are prepared in the same fashion as other nucleotide analogue bases described in the literature. Similarly, conventional phosphodiester linkages are prepared from nucleotide analogues containing coupling groups D and $D^1$ described above. The compounds of this invention then are incorporated into the desired oligonucleotide by known methods of in vitro synthesis described in the referenced methods. Alternatively, polycyclic substructure-substituted nucleotide triphosphates may be incorporated into oligonucleotides as cytosine analogues by DNA polymerase or reverse transciptase in vivo or in vitro (see Ward, U.S. Pat. No. 4,711,955). In this case, $R^1$ is ribosyl or deoxribosyl triphosphate, or a triphosphorylated analogue thereof recognized by DNA polymerase or reverse transcriptase which is then incorporated into an oligonucleotide by template-directed transcription.

Synthesis of oligomers containing about 3 or more nucleotide residues is preferably accomplished using synthons such as dimers (which contain substitute or diester linkages) or trimers (each carrying a terminal coupling group suitable for use with amidite, H-phosphonate or triester chemistries.) The synthon is then linked to the oligomer or another synthon via a phosphodiester or phosphorous-containing substitute linkage.

Oligomers containing methylphosphonate and phosphodiester linkages are readily prepared by solid-phase oligomer synthesis techniques. A description of modifications useful in the synthesis of phosphorothioate linked oligomers are found, for example, in EP 288,163, wherein the oxidation step in solid phase automated synthesis using amidite chemistry can be independently adjusted at any step to obtain the phosphorothioate. An alternate method for synthesis of oligomers with phosphorothioate linkages, via hydrogen phosphonate chemistry, has also been described (Froehler "NAR" 14:5399, 1986). Sulfuriation is accomplished using reagents such as tetraethylthiuram disulfide, dibenzoyl tetrasulfide, thiophosphoric acid disulfide, 3H-1, 2benzodithiol-3-one 1,1-dioxide and the like as described (Vu, "Tet Lett" 26:3005, 1991; Rao, "Tet Lett" 33:4839, 1992; U.S. Pat. No. 5,151,510; Iyer, "JOC" 55:4693, 1990; Dahl, "Sulfur Reports" 11:167, 1991). These sulfurization reagents are used with either phosphoramidite or hydrogen-phosphonate chemistries. Synthesis of phosphorothioate oligomers having controlled stereochemistry is used to generate stereoregular invention oligomers as described (EP 506, 242). Thionomethyl phosphonate is prepared with methylphosphonamidite followed by sulfurization as described (Roelen, "Tet Lett" 33:2357, 1992) or with the sulfurization reagents described above.

Uses for the Compounds of this Invention

The compounds of this invention find uses in the diagnostic, analytic and therapeutic fields, or as intermediates in the preparation of compounds useful in such fields.

The linker-substituted compounds of structure (1) are useful as intermediates in the preparation of the labeled biopolymers of structure (1), wherein a biopolymer is rendered fluorescent or otherwise detectably labeled by linkage to the polycyclic substructure. It is most convenient, however, to use the appropriate structure (1) compounds as monomers in the preparation of structure (1) nucleic acids or oligonucleotides. The labeled biopolymers are employed in diagnostic assays or preparative procedures in the same fashion as other fluorophor-labeled biopolymers, e.g. in fluorescence polarization methods, fluorescence activated cell sorting, competitive-type EMIT immunoassays and the like.

The monomers are of particular use in preparing oligonucleotides for diagnostic or therapeutic use. Since oligonucleotides having 2 or more adjacent nucleotides or nucleotide analogues bearing the polycyclic substructure exhibit greatly increased Tm, such oligonucleotides are particularly useful in therapeutic or diagnostic utilities where highly stable duplex hybridization structures are desired. Since these oligonucleotides are fluorescent, changes in the oligonltide fluorescence can be followed as the oligonucleotide binds to complementary nucleic acid or oligonucleotide sequences. These changes are detectable as modifications in energy transfer, e.g., fluorescence quenching or shifts in activation or emission wavelength(s).

The polycyclic substructure labeled oligonucleotides are employed in diagnostic or analytic methods in the same fashion as other labeled oligonucleotides. For example, the oligonucleotides are used in hybridization methods in which an antibody capable of binding base-paired structure (1) is used to detect binding of the oligonucleotide to a target nucleic acid sequence. In addition, changes in fluorescent character can be assayed as described above. Following the general method of EP 70,685, at least 2 polycyclic substructure labeled oligonucleotides are used in a hybridization assay. One oligonucleotide is labeled at its 3' end with a polycyclic substructure containing nucleotide while the other nucleotide is labeled at its 5' end with the same or another polycyclic substructure or with a different fluorophore such as fluorescein or rhodamine capable of energy transfer. The two oligonucleotides recognize a complementary sequence in which the 3' end of the target sequence binds the oligonucleotide bearing the 3'-terminal fluorophore and the adjacent 5' sequence of the target binds to the oligonucleotide bearing the 5' terminal fluorophore. Binding is assayed by measuring a change in fluorescence of either or both of the oligomers when they bind in tandem according to the illustrated model. In other embodiments only a single labeled oligonucleotide is employed in the hybridization method. The oligonucleotides of this invention thus are useful in solution phase hybridization diagnostics, i.e., it is not necessary to perform a phase separation in order to detect labeled oligonucleotide binding.

Structure (1) monomers, when triphosphorylated and containing $R^1$ ribose or deoxyribose derivatives that are chain terminating (e.g. where $R^{17}$, $R^{18}$ and both $D^1$ are not hydroxyl), are useful in methods for fluorescent chain-terminating dideoxynucleotide sequencing in the same general fashion as ddNTPs having other linker-attached fluorophores.

Since the compounds of structure (1) are, capable of participating in Watson-Crick base pairing they will bind to nucleic acids and therefore are useful in detecting the presence of nucleic acids containing guanosine.

Structure (1) oligonucleotides capable of forming high melting duplexes with complementary sequences are useful in numerous processes, including antisense or codeblocking utilties in vivo or in vitro as well as diagnostics. High melting duplexes are those having melting temperatures substantially above the melting temperatures of oligonucleotide or nucleic acid duplexes of the same sequence that contain the ordinary, naturally occuring bases, e.g., adenosine, cytidine, uridine, guanosine, thymidine and the like. "Substantially above" means that the derivative oligonucleotide, when hybridized with its complementary sequence, will not dissociate from the duplex until the temperature is raised from about 2 to 40° C., ordinarily about 8 to 40° C., above the dissociation temperature of the same oligonucleotide having the analogous normal A, C, U, G or T bases, but to no greater temperature than about 95° C. This is known as the Δ Tm. Ordinarily, Δ Tm is measured by comparing control oligonucleotide binding to complementary RNA with the binding of test oligonucleotide to the same RNA, following the method described in Jones et al., "JOC" 58:2983 (1993).

The ability of the compounds of this invention to form high melting duplexes is shown in the following data. The polycyclic cytidine derivatives of this invention were incorporated into two test 15 mer oligonucleotides by conventional phosphodiester chemistry. The test sequence is complementary to the sequence of "compound 26" RNA (i.e., AGAGGGAGAGAAAAA; SEQ ID NO:1) described in Jones et al., "JOC" op cit. In one test oligonucleotide ("homo-3"; SEQ ID NO:2), 3 of the designated polycycles were inserted into the olignucleotide in tandem, i.e., as XXX (the C triplet in the test oligo). In the other ("alt-3"; SEQ ID NO:3), the 3 polycycles were not adjacent but instead were separated by from 1 to 5 bases (the nonadjacent cytidine bases in the test oligo). The remainder of the bases were C and T as deduced from the reference sequence. A comparison oligonucleotide containing a 5-propyne deoxy C triplet (analogous to the homo-3 oligonucleotide containing the bases of this invention, "5-Propyne dC (homoC)") was prepared and tested in the same assay system. ΔTm was calculated against the Tm of a control oligonucleotide containing the same sequence, but with 5-methyl deoxy C in place of the cytidine bases of the test oligonucleotides. The structures of the test polycycles are shown below, as are their designations (e.g., "benzene tricyclic C") for the Tm's shown in the following table ("dR" is deoxyribose).

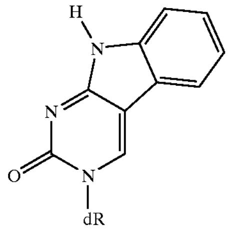

Benzene Tricyclic Cytidine

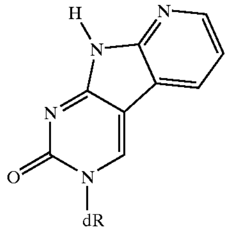

2-Pyridine Tricyclic Cytidine

-continued

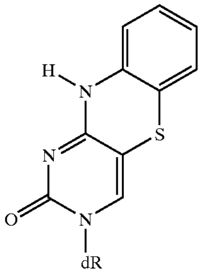

Phenothiazine Tricyclic Cytidine

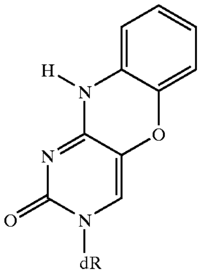

Phenoxazine Tricyclic Cytidine

TABLE II

Tricyclic Cytidine Derivatives for Enhanced RNA Affinity

| Cytidine Modification | Δ Tm RNA (° C.) | Δ Tm Substitution (° C.) |
|---|---|---|
| 5-Propyne dC (homo-3) | +8.0 | +2.7 |
| Benzene Tricyclic dC (homo-3) | +8.0 | +2.7 |
| Benzene Tricyclic dC (alt-3) | 0.0 | 0.0 |
| 2-Pyridine Tricyclic dC (homo-3) | +7.5 | +2.5 |
| 2-Pyridine Tricyclic cD (alt-3) | 0.0 | 0.0 |
| Phenathiazine Tricyclic dC (homo-3) | +13.0 | +4.3 |
| Phenathiazine Tricyclic dC (alt-3) | +4.5 | +1.5 |
| Phenoxazine Tricyclic dC (homo-3) | +15.0 | +5.0 |
| Phenoxazine di-methyl Tricyclic dC (homo-3)* | +17.5 | +5.8 |
| Phenoxazine Tricyclic dC (alt-3) | +6.5 | +2.2 |

Tm for the tabulated oligonucleotides is obtained by adding 62.5° C. to the Δ Tm figure

*Example G 3.

This data demonstrates the enhancement in melting point afforded by the oligonucleotides of this invention, particularly those having tandem arrangements of the novel bases In general, such tandem arrangements will contain from 2 to about 10 polycyclic bases, which can be the same or different polycycles but generally are the same polycycle. They also optionally are copolymerized with purine or pyrimidine bases containing known alkynyl substitutions (PCr 92/10115 and USSN 08/050,698), in particular pyrimidine bases substituted at the 5 position with a carbon atom which is bonded to another atom by a Pi bond, or the fluorescent cytosine derivatives of Inoue et al (op cit)

The phenothiazine and phenoxazine deoxyriboside compounds have excitation and emission wavelengths of Ex380 nM/EM 492nM and Ex360 nM/EM450nM, respectively, and are intensely fluorescent. They compounds remain fluorescent upon incorporation into oligonucleotides and are visible intracellularly when bound to target sequences after direct injection in accord with known methods. The test phenoxazine oligonucletides bind to target upon direct injection at an $IC_{50}$ of 5–10 microM, with a betagalactosidase control remaining unaffected, and therefore are useful in antisense methods for inhibition of translation of target RNAs.

The compounds of this invention, or other oligonucleotides capable of forming high melting duplexes (e.g. the Pi bonded bases discussed above), are useful in improved methods for polymerase chain reaction ("PCR") or ligase chain reaction ("LCR") amplification and detection of nucleic acids. In one embodiment, the high melting oligonucleotides are used as one or both primers in classical PCR or as probes in LCP Particularly in PCR processes, the elevated melting temperature of duplexes with high melting primers avoids the need to thermally cycle the reaction because at these elevated temperatures (about 68 to 95° C., preferably greater than about 75° C.; the derivative primer will continue in at least some proportion to anneal to the target but extension product will not. Ordinary primers will not hybridize and the polymerase will not initiate transcription until the reaction mixture is cooled to a level at which the primer will anneal to the target sequence (usually, about 55° C.): The elevated temperature that is chosen for use with the high-melting derivative oligonucleotides (a temperature suitable for all of annealing extension and melting) is one at which a substantial proportion of the extended primer population (about 10 to 90 mole %) is found dissociated from the target, but sufficient unextended primer is bound to permit extension. Optimally, this is about from 85 to 95° C., ordinarily 92 to 95° C. Alternatively, the optimal temperature is determined empirically by simply selecting a range of temperatures within the melting range of the extended sequence, but within the annealing range of the derivative primers, and measuring the amount of amplification product to achieve satisfactory levels for the diagnostic or preparative processes at hand.

It will be understood that the optimal temperature will vary considerably depending upon the derivative bases chosen, whether they are adjacent or separated by other bases, the number of bases in the primers (the highest annealing temperatures are found with primers having greater than about 18 bases or base analogues), the proportions of pyrimidines and purines and the like. The heat stable polymerase useful in this system is for example Taq polymerase or other suitable heat stable enzyme. Thus, whatever the optimum temperature chosen, the amplification and priming reactions are conducted conventionally but at a substantially constant temperature.

Not only do the oligomers of this invention faciliate PCR or LCR processes, the fluorescent properties of the primers also facilitate detection of the extension products. The extension products are readily separated from the unextended primers, e.g. on the basis of molecular weight, and detected by their fluorescence, thereby avoiding staining with agents such as ethidium bromide. In some embodiments, the fluoresence is enhanced by using NTP's comprising the fluorescent substructures of this invention in primer extension so that the fluorescent N*Ts are incorporated into the extension products as well. The polycyclic substructure used in the NTP's may be the same or different than the one incorporated into the primers.

All citations are hereby expressly incorporated by reference. The following examples are illustrative and do not limit the scope of this invention.

EXAMPLE 1

Representative Application of the Scheme of FIG. 5

A. 5-(2-N-tert-butoxycarbonyl aniline) 5'-dimethoxytrityl-2'-deoxyuridine (DMT-AU).

The synthesis of N-(tert-butoxycarbonyl)-2-(trimethylstannyl) aniline (BocSnA) was as reported in Salituro and McDonald, J. Org. Chem. 53, 6138–6139, 1988.

1.5 g of 5iodo-2'-deoxyuridine, 5 g of BocnA and 50 mg of palladium dichloride bistriphenyl phosphine were dissolved in 5 ml DMF and sealed under $N_2$. The reaction was heated for 16 h at 50° C. The reaction was cooled, diluted with ETOH, 1 ml of triethylamine was added and filtered through Celite. The clear solution was then concentrated under reduced pressure and flash chromatographed on silica gel with a gradient of methanol in methylene chloride (0%–10%). Upon concentration the nucleoside was rendered anhydrous by pyridine addition and evaporation which was subsequently reacted with 880 mg of dimethoxytrityl chloride in 10 ml of pyridine for 1 h at 20° C. The reaction was quenched with methanol and partitioned into methylene chloride and $H_2O$. The organic phase was concentrated under reduced pressure and purified by flash chromatography on silica gel eluting with a gradient of isopropanol in methylene chloride (0%–4%). The yield was 720 mg of DMT-AU.

B. Dimethoxytrityl benzopyrimidine polycyclic nucleoside 700 mg of DMT-AU was treated with 3 ml of trimethylsilyldimethyl amine in 3 ml $CH_3CN$ for 2 h at 20° C. followed by evaporation at reduced pressures redissolving in $CH_3CN$ and reevaporation 2 times. The residue was then dissolved in 7 ml $CH_3CN$ and 0.67 ml of triethylamine, 11 mg of 4-dimethylaminopyridine and 420 mg of mesitylenesulfonylchloride were added under $N_2$ and stirred for 4 h at 20° C. 0.72 ml of 1,8 diazabicyclo [5.4.0] undec-7-ene was added and stirred 30° at 20° C. followed by 0.015 ml of $H_2O$ and stirring for 1 h. Workup consisted of partitioning between methylene chloride and 0.5 M aqueous dibasic sodium phosphate. Evaporation under reduced pressure of the organic phase followed by silica gel chromatography using an isopropanol gradient in methylene chloride (0%–5%) yielded 300 mg of tricyclic nucleoside. The nucleoside was converted into its 3' hydrogen phosphonate derivative and incorporated into oligonucleotides by standard procedures (see Jones, et. al., J. Org. Chem. 58, 2983–2991, 1993.)

EXAMPLE 2

Representative Application of the Scheme of FIG. 6

A. 2-Fluoro3trimethylstannyl-pyridine (FSnP)

Metalation of 2-fluoropyridine was performed as described in Estel, Marsais and Queguiner, J. Org. Chem. 53, 2740–2744, 1988. The lithium anion was quenched with 1 eq. of trimethyl tin chloride in THF (1 M) at −78° C. and stirred for 30', quenched with 1 M sodium bicarbonate and extracted with ethyl acetate. Upon $Na_2SO4$ drying and evaporation under reduced pressure the resulting oil was used without further purification.

B. Deoxycytidine-5-(3-(2-fluoropyridine))-5dimethoxytrityl-2'-deoxycytidine (DMT.FPdC)

500 mg of 5-Iodo-2'deoxycytidine was heated at 100° C. in 4 ml DMF and 2 ml DMF dimethyl acetal After 2 h. the reaction was cooled and concentrated under reduced pressure. The residue was dissolved in 4 ml DMF, 2 ml FSnP and palladium chloride bistriphenylphosphine was added under $N_2$ and heated for 16 IL at 50° C. The reaction cooled and 4 ml of ammonia-saturated methanol was added and stirred for 4 h. at 20° C. The reaction was concentrated under reduced pressure and precipitated into anhydrous ethyl ether. The precipitate was dried and dissolved in pyridine, evaporated under reduced pressure and redissolved in 4 ml pyridine. 400 mg of dimethoxytritylchloride was added and after 30 minutes at 20° C., the reaction was quenched with MeOH, extracted with methylene chloride and $H_2O$. The organic layer was concentrated and purified by flash chromatography on silica gel using a methanol gradient in methylenechloride (5–10%).

C. Dimethoxytrityl-2-pyridine Polycyclic Nucleoside 0.3 ml of dry diisopropylamine was combined with 4 ml dry THF under $N_2$ and cooled to 0° C. 1.2 ml of 1.7 M butyllithium in THF was added dropwise and the reaction was stirred for 5 min. 200 mg of DMT-FPdC in 10 ml of dry ThP was then added dropwise. After 1 h. at 0° C. the reaction was quenched with 1M sodium bicarbonate and extracted with ethyl acetate. The organic layer dried with $Na_2SO_4$ and was concentrated under reduced pressure and purified by flash chromatography on silica gel using a gradient of methanol (5–1%) in methylene chloride. After concentration under reduced pressure the compound was converted to H-phosphonate derivative by standard procedures (see Jones, et. al., “JOC” 58, 2983–2991, 1993.)

EXAMPLE 3

Figure 8A:
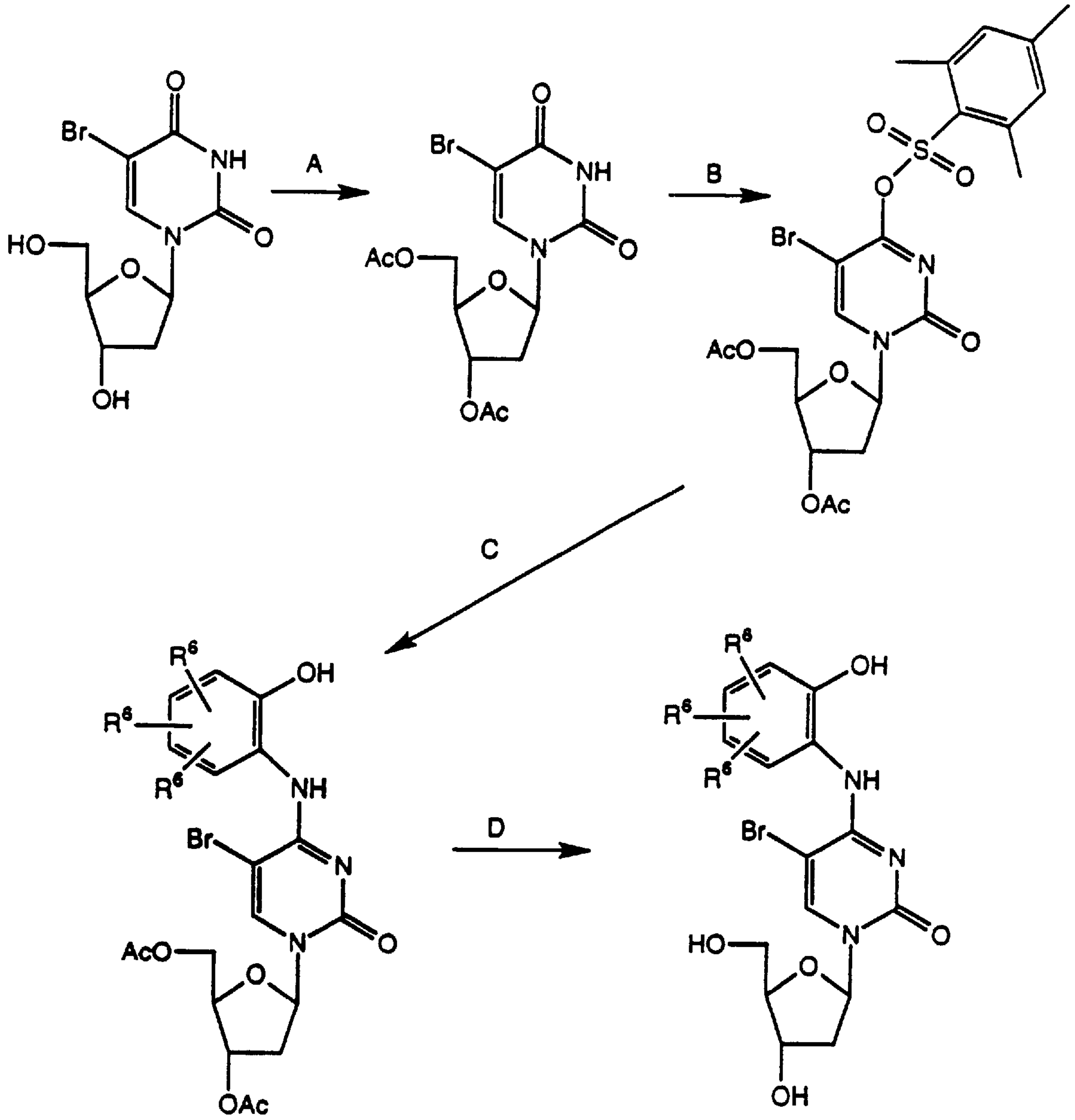
Figure 8B:
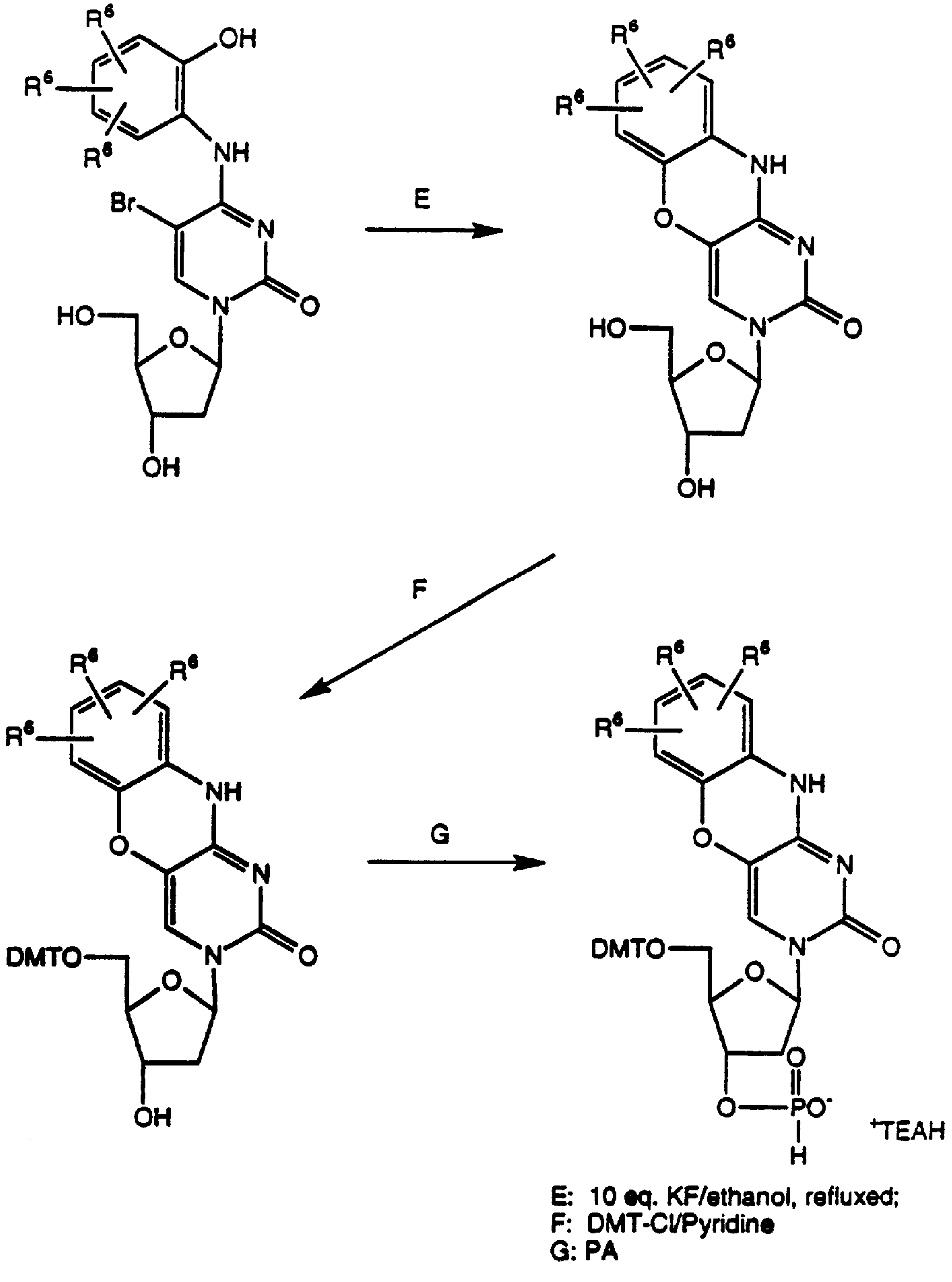
Figure 9:
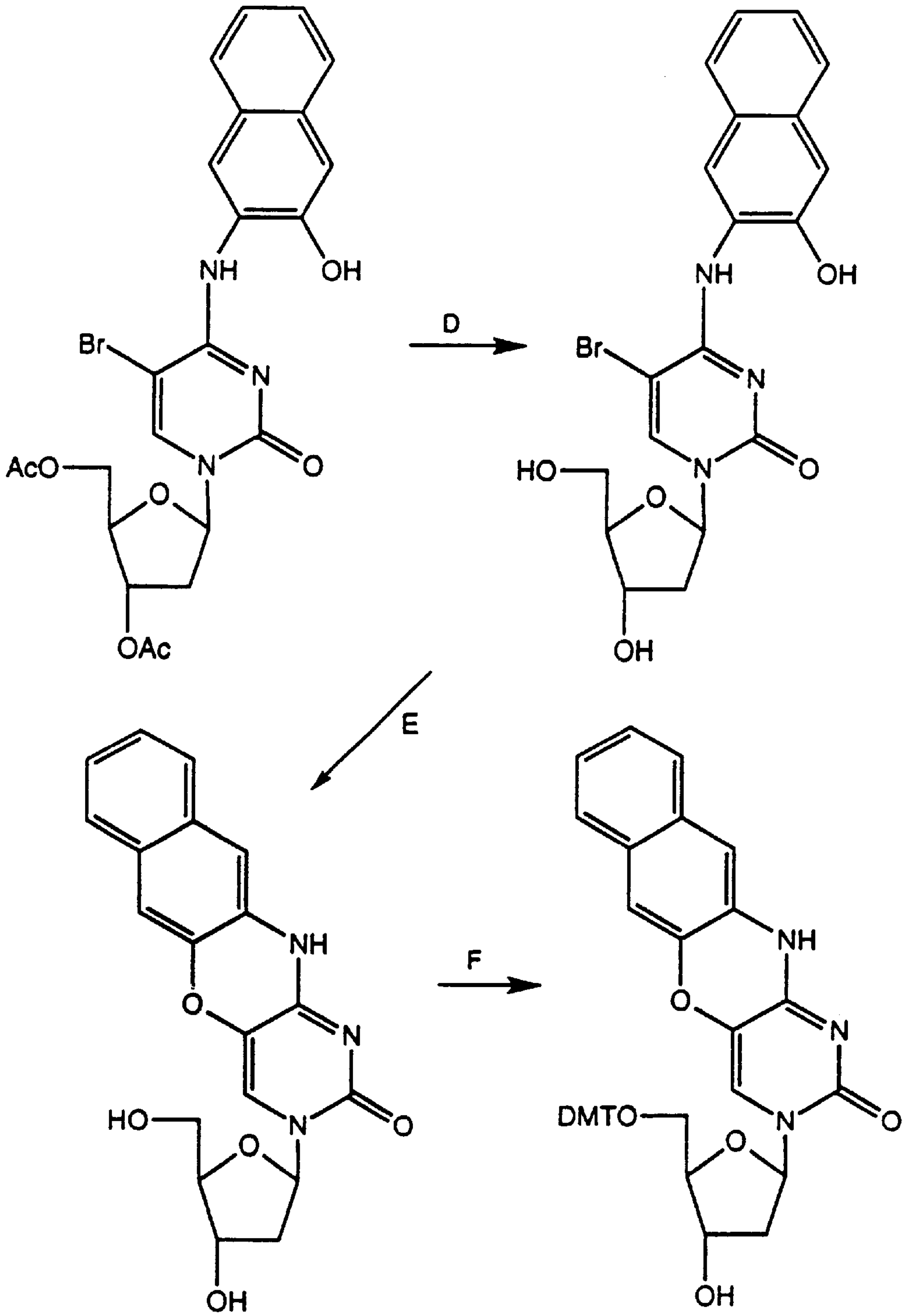
Figure 10A:
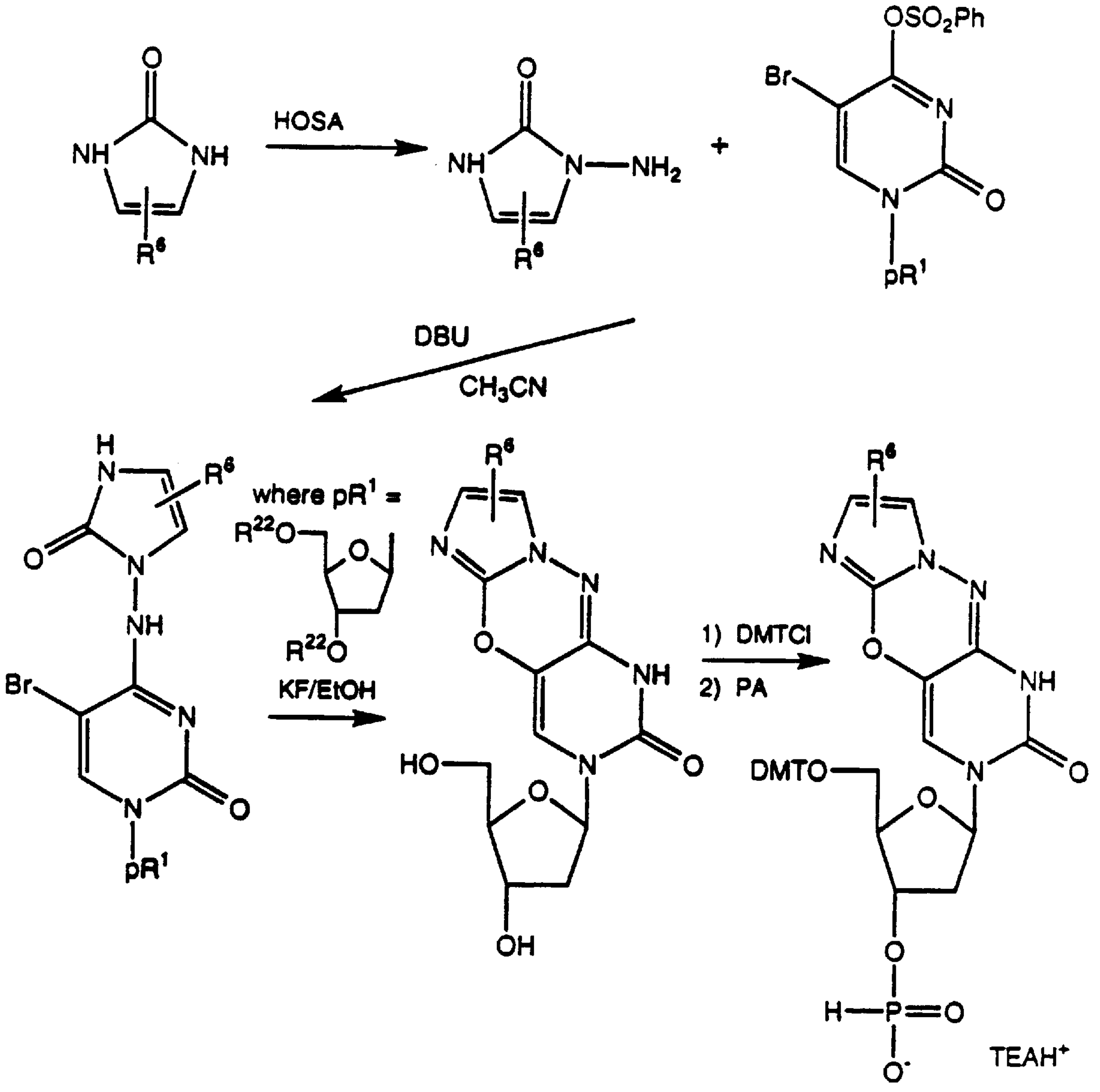
Figure 10B:
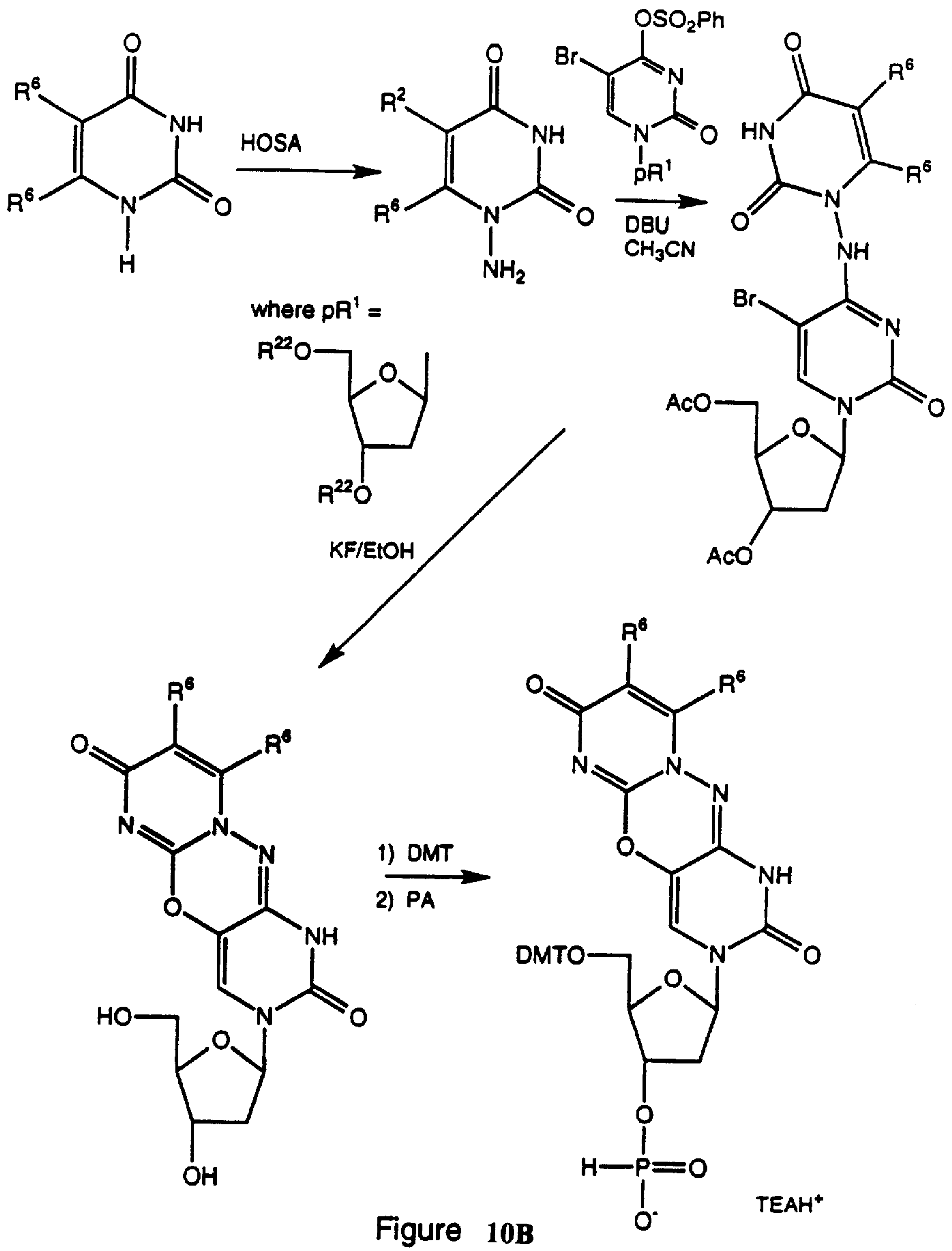

Representative Application of the Scheme of FIGS. 8A and 8B

A. 3',5'-Diacetyl-5-bromo-2'-deoxyuridine

5-Bromo-2'-deoxyuridine (7.3 g; 23.7 mmol) was dissolved in pyridine (30 ml) and treated with acetic anhydride (10 g; 95 mmol) at room temperature for 3 h. The reaction was quenched with methanol and concentrated. The residue was partitioned between $CH_2Cl_2$ and saturated $NaHCO_3$ aq. solution. The organic layer was separated, dried-over $MgSO_4$, then concentrated to give the title compound quantitatively.

B.1. 5-Bromo3',5'-diacetyl-$N^4$-(2-hydroxyphenyl)-2'-deoxycytidine

To a solution of 3',5-diacetyl-S-bromo-2'-deoxyuridine (8.5 g; 21.7 mmol), methylene chloride (100 ml), triethylamine (8.8 g; 87 mmol) and DMAP (0.13 g) was added 2-mesitylsulfonyl chloride (9.5 g; 43.4 mmol). After stirring at room temperature for 18 h DBU (6.6 g; 435 mmol) and 2-aminophenol (95 g; 87 mmol) were added and the solution was stirred for 1 hr. The reaction mixture was concentrated and the residue was partitioned between ethyl acetate and saturated sodium bicarbonate aq. solution. The organic layer was purified by flash column chromatography on silica gel to yield the title compound.

B.2. 5-Bromo-3',5'-diacetyl-$N^4$-(2-hydroxy-m-nitrophenyl)-2'-deoxycytidine

To a solution of 3', 5'-diacetyl-5-bromo-2'-deoxyuridine (4.8 g; 12 mmol), methylene chloride (50 ml), triethylamine (5.0 g; 50 mmol) and DMAP (0.10 g) was added 2-mesitylsulfonyl chloride (5.2 g; 24 mmol). After stirring at room temperature for 4 h., DBU (3.6 g; 24 mmol) and 2-amino4-nitrophenol (7.4 g; 48 mmol) were added and the solution was stirred for 3 h. The reaction mixture was concentrated and the residue was partitioned between ethyl acetate saturated sodium bicarbonate. The organic layer was purified by flash column chromatography on silica gel. The isolated product had some impurity and was triturated with ethyl acetate. The yellowish precipitate was filtered off and washed with methylene chloride to yield the title compound.

B.3. 5Bromo-3',5'-diacetyl-$N^4$-(2hydroxy-3,5-dimethylphenyl)2'-deoxycytidine

The title compound was synthesized by the way of synthesis of compound 3.B.1. except that the reaction used 2-amino4,6 dimethylphenol in place of 2-amino4-nitrophenol. The reaction mixture was purified by flash column chromatography on silica gel to afford the desired compound which containing some impurity and was used for the next reaction without further purification.

B.4. 5-Bromo-3',5'-diacetyl-$N^4$-[2-(3-hydroxynaphthyl)]-2'-deoxycytidine

To a solution of 3',5'-diacetyl-5-bromo-2'-deoxyuridine (4.0 g; 10 mmol), methylene chloride (50 ml), triethylamine (4.0 g; 40 mmol) and DMAP (0.1 g) was added 2-mesitylsulfonyl chloride (4.4 g; 20 mSol). After stirring at room temperature for 6 h DBU (3.0 g; 20 tnmol) and 3-amino-2-naphthol (6.4 g; 40 mmol) were added and the solution was stirred for 4 h. at room temperature. The reaction mixture was concentrated, the residue was dissolved in ethyl acetate and washed with saturated sodium bicarbonate aq. solution, but the title compound was precipitated from solution. The precipitates were filtered off and washed thoroughly with ethyl acetate, then methylene chloride, and dried. A small quantity of title compound also was obtained from the filtrate.

C.1. 5-Bromo-$N_4$-(2-hydroxyphenyl)-2'-deoxycytidine

5-Bromo-3',5'-diacetyl-$N^4$-(2-hydroxyphenyl)-2'-deoxycytidine (Ex.3.B.) (4.3 g; 8.9 mmol) was treated with saturated ammonium in methanol at room temperature for 3 h. and concentrated to dryness. The residue was triturated with methylene chloride/hexane (1/1). The off-white solid was filtered off, washed thoroughly with methylene chloride/hexane and dried.

C.2. 5-Bromo-$N^4$-(2-hydroxy-m-nitrophenyl)-2'-deoxycytidine

The title compound was prepared from compound 3.B.2. by the way of synthesis of compound 3.C1.

C.3. 5-Bromo-$N^4$-(2-hydroxy-3,5-methylphenyl )-2'-deoxycytidine

The crude compound of 3.C2. was treated with 100 ml of saturated $NH_3$ in methanol at room temperature for 5 h. then concentrated to dryness. The residue was partitioned between methylene chloride and saturated sodium bicarbonate aq. solution The organic phase was isolated, dried and purified by flash column chromatography on silica gel affording the title compound.

C.4. 5-Bromo-$N^4$-[2-(3-hydroxynaphthyl)]-2'-deoxycytidine

The compound produced in example 3.B.4. (3.1 g; 5.8 mmol) was treated with saturated $NH_3$ in methanol (150 ml) at room temperature for 6 h. The reaction mixture was concentrated and the residue was triturated with methylene chloride/ethyl acetate. The precipitate was filtered off, washed thoroughly with methylene chloride, dried, yielding 25 g, 96%.

D.1. 2'-Deoxyphenoxazine Tricyclic dC

Potassium fluoride (43 g; 75 mmol) was added to an ethanol solution (150 ml) of the compound prepared in example 3.C.1. (3.0 g; 7.5 mmol). The resulting solution was refluxed for 3 days. The solution was cooled to room temperature, some precipitate was filtered off and the filtrate was concentrated to dryness and used for Example 3.F.1. without further purification.

D.2. 2'-Deoxy-p-nitrophenoxazine Tricyclic dC

A solution of the compound of Example 3.C.2. (24 g; 5.4 mmol), potassium fluoride (3.1 g; 54 mmol), ethanol (100 ml) and DMSO (30 ml) was placed in a bomb and reacted at 120° C. for 3 days. The reaction mixture was concentrated and purified by flash column chromatography on silica gel. The crude product was used for Example 3.E. without further purification.

D.3. 2'-Deoxy-2,4-dimethylphenoxazine Tricyclic dC

The title compound was synthesized by the same procedure as in Example 3.D.1., except that the dimethylphenyl compound of Example 3.C3. was used as starting material.

D.4. 2'-Deoxy-naphthoxazene Tricyclic dC

The compound of example 3.C.4. (2.4 g; 53 mmol) and potassium fluoride (3.1 g; 53 mmol) were refluxed in ethanol (100 ml) for 4 days. The reaction mixture was cooled to room temperature and concentrated to dryness, yielding the title compound.

E. 3',5'-Diacetyl-2'-deoxy-p-nitrophenoxazine

The crude product of Example 3.D.2. (0.3 g) was dissolved in pyridine (10 ml) and reacted with acetic anhydride (3 ml) at room temperature for 3 h. The mixture was quenched with methanol, concentrated and partitioned between methylene chloride and saturated sodium bicarbonate aq. solution The organic phase was purified by flash column chromatography on silica gel affording the title compound.

F.1. 5'-O-Dimethoxytrityl-2'-Deoxyphenoxazine Tricyclic dC

The crude product of Example 3.D.1. was dissolved in pyridine (35 ml) and treated with 4,4'-dimethoxytrityl chloride (5 g; 14.7 mmol) at room temperature for 1.5 h, concentrated. The residue was dissolved in methylene chloride and washed with saturated sodium bicarbonate aq. solution. The organic phase was isolated, dried, concentrated, then purified by flash column chromatography on silica gel to yield the title compound. The nucleoside was converted into its 3' hydrogen phosphonate derivative and incorporated into oligonucleotides by standard procedures.

F.2. 5'-O-Dimethoxytrityl-2'-deoxy-4-nitrophenoxazine Tricyclic dC

The compound of Example 3.E. (0.27 g; 0.608 mmol) was treated with saturated $NH_3$ in methanol (20 ml) at room temperature for 4 h, then concentrated. The residue was dissolved in pyridine (10 ml) followed by addition of 4,4'-dimethoxytrityl chloride (0.25 g; 0.73 mmol). After stirring at room temperature for 3 h., the reaction mixture was concentrated, then partitioned between methylene chloride and saturated sodium bicarbonate aq. solution. The organic phase was dried and purified by flash column chromatography on silica gel, affording the title compound.

F.3. 5'-O-Dimethoxytrityl-2'-deoxy-2,4-dimethylphenoxazine Tricyclic dC

The compound of Example 3.D.3 ( 0.3 g; 0.87 mmol) was dissolved in pyridine (5 ml) followed by addition of 4,4'-dimethoxytrityl chloride (0.4 g; 1.2 mmol) and DMAP (10 mg). The reaction mixture was stirred at room temperature for 2 h., concentrated, then partitioned between methylene chloride and saturated sodium bicarbonate aq. solution. The organic phase was isolated, dried and purified by flash column chromatography on silica gel affording the title compound. Unreacted compound (85 mg) was recovered from aq. solution.

F.4. 5'-O-Dimethoxytrityl-2'-deoxy-2-naphthoxazene Tricyclic dC

The compound of Example 3.D.4. was dissolved in pyridine (15 ml) followed by addition of 4,4'-dimethoxytrityl chloride (3.1 g;, 9.1 mmol) and DMAP (15 mg). After stirring at room temperature 3 h., the reaction mixture was concentrated, then partitioned between methylene chloride and saturated sodium bicarbonate aq. solution. The organic solution was isolated, dried over $MgSO_4$, purified by flash column chromatography on silica gel affording the title compound G. 5'-O-Dimethoxytrityl-2'-deoxy-phenoxazine Tricyclic dC The nucleosides (3.F.1., 3.F.2, 3.F.3., 3.F.4.) were converted into their 3' hydrogen phosphonate derivatives and incorporated into oligonucleotides by standard procedures.

EXAMPLE 4

Figure 7:
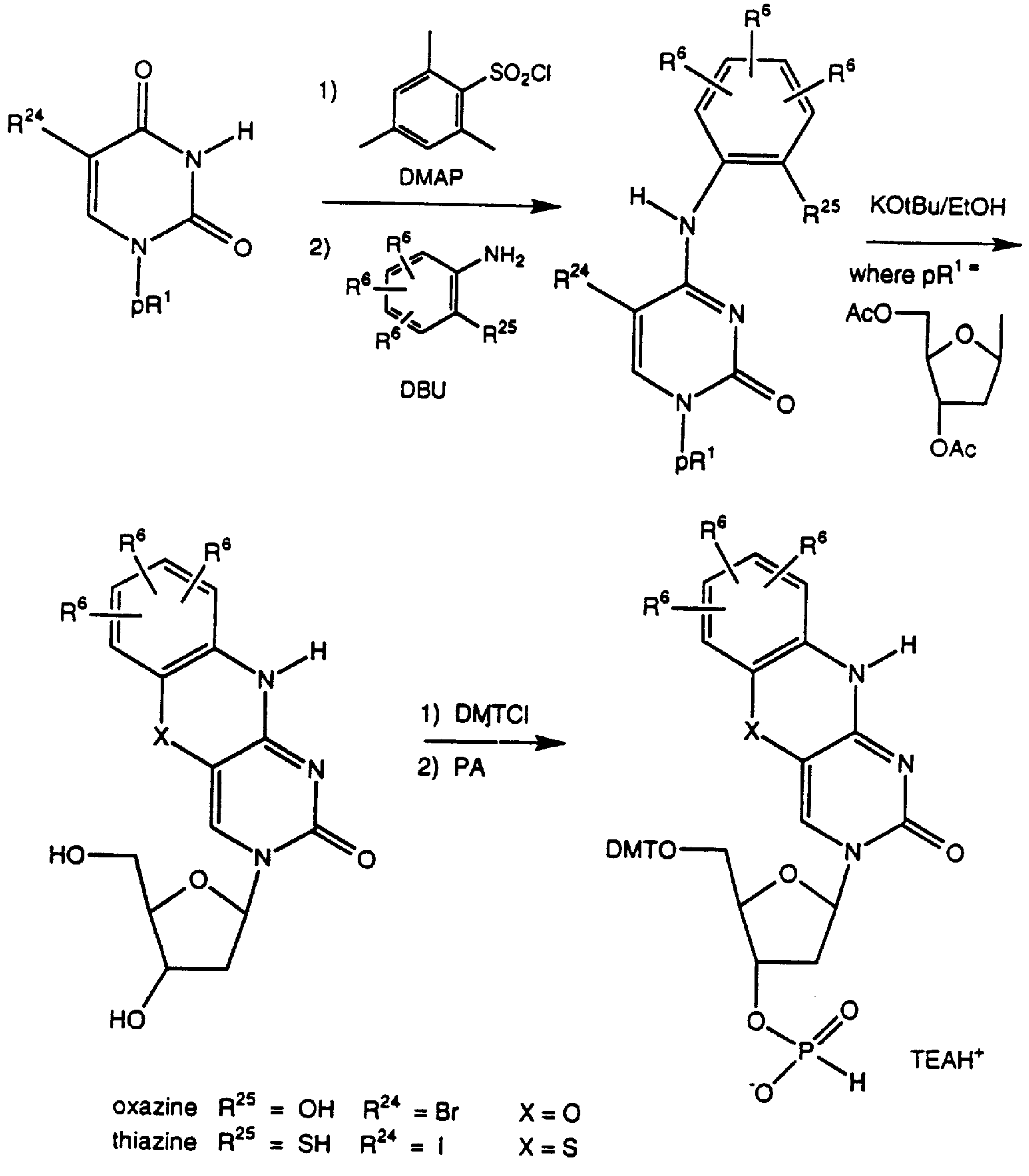

Representative Application of the Scheme of FIG. 7

A.1. 5-Iodo-3',5'-diacetyl-$N^4$(2-mercaptophenyl)-2'-deoxycytidine

To a solution of 3',5'-diacetyl-5-iodo-2'-deoxyuridine (2.19 g, 5.00 mmol) acetonitrile (ACN, 75 ml), triethylamine (TEA, 6.96 ml, 50.0 mmol) and DMAP (0.15 g, 1.25 mmol) was added mesitylsulfonyl chloride (2.19 g, 10.0 mmol). After stirring at ambient temperature for 18h, DBU (2.14 ml, 10.0 mmol) and 2-aminothiophenol was added (2.14 g, 20.0 mmol) and the solution was stirred for 1 h. The reaction mixture was concentrated and the crude product was partitioned between ethyl acetate (EA, 200 ml) and saturated aqueous sodium bicarbonate (SASB, 200 ml). The organic layer was dried ($Na_2SO_4$) and concentrated on the rotary evaporator. The crude product was purified by flash chromatography on silica gel [1–5% 2-propanol/dichloromethane (DCM)] to deliver the product $^1H$ NMR ($CDCl_3$) δ2.10 (s, 3H), 2.15 (m, 1H, 2.17 (s, 3H 2.77 (ddd, 1H, J=2.2, 5.2,15.1 Hz), 4.14 (bs, 1H), 4.35 (m, 3H), 5.20 (m, 1H), 6.13 (t, 1H, J=6.5 Hz), 6.78 (m, 2H), 7.30 (m, 2H), 8.05 (s, 1H).

A.2. 5-Bromo-3',5'-diacetyl-$N^4$-hydroxyphenyl)-2'-deoxycytidine

To a solution of 3',5'-acetyl-5-bromo-2'-deoxyuridine (1.79 g, 5.00 mmol) acetonitrile (ACN, 75 ml), triethylamine (TEA, 6.96 ml, 50.0 mmol) and DMAP (0.15 g, 125 mmol) was added mesitylsulfonyl chloride (2.19 g, 10.0 mmol). After stirring at ambient temperature for 1 h, DBU (2.14 ml, 10.0 mmol) and 2-aminophenol were added (2.18 & 20.0 mmol) and the solution was stirred for 1 h. The reaction mixture was concentrated and the crude product was partitioned between ethyl acetate (EA, 200 ml) and saturated aqueous sodium bicarbonate (SASB, 200 ml). The organic layer was dried ($Na_2SO_4$) and concentrated on the rotary evaporator. The crude product was purified by flash chromatography on silica gel [20–40–60–80–100% EA/Hexanes]. The product fractions were concentrated, and the product was triturated from EA.

B. 2'-Deoxyphenothiazine

A solution of diacetate from Step A (600 mg, 1.10 mmol), potassium tert-butoxide (1.0 M in THF, 2.20 ml, 220 mmol) and abs. ethanol (25 ml) was heated at reflux for 0.5 h. The solution was allowed to cool to ambient temperature and treated with acetic acid (0.5 ml). The solution was concentrated; toluene (50 ml) was added, and the solution was again concentrated. The crude product was purified by flash chromatography on silica gel (2–10% Methanol (ME)/DCM) to afford the phenothiazine. $^1$H NMR ($d_6$DMSO) δ2.02 (m, 1H), 2.11 (m, 1H), 3.56 (dq, 2H, J=3.5, 12.0 Hz), 3.77 (m, 1H), 4.19 (m, 1H), 6.06 (t, 1H, J=63 Hz), 6.92 (m, 2H), 7.06 (m, 2H), 7.82 (s, 1H).

These compounds were dimethoxytritylated C and phosphitylated D by standard procedures.

C. 5'-O-DMT-2'-deoxyphenothiazine (from FIG. 7)

$^1$H NMR ($d_6$ DMSO) δ2.17 (m, 2H), 3.14 (dd, 1H, J=1.6, 9.7 Hz), 3.23 (dd, 1H J=4.6, 10.4 Hz), 3.74 (s, 6H), 3.91 (m, 1H), 426 (m, 1H), 531 (d, 1H, J=4.4 Hz), 6.09 (t, 1H, J=6.4 Hz), 6.91 (m, 4H), 7.07 (m, 1H), 7.20–7.41 (m, 12H), 7.59 (s, 1H), 10.46 (s, 1H).

D. 5'-DMT-3'-H-phosphonate-2'-deoxyphenothiazine, triethyl ammonium salt $^1$H NMR (d6 DMSO) δ1.15 (t, 9H, J=7.23 Hz), 2.23 (m, 1H), 236 (m, 1H), 3.00 (q, 6H, J=7.2 Hz), 3.15 (dd, 1H, J=20, 9.95 Hz), 3.27 (dd, J=4.4, 10.5 Hz), 3.72 (s, 6H), 4.08 (m, 1H), 4.70 (m, 1H), 6.09 (t, 1H, J=6.4 Hz), 6.60 (d, 1H, J=584 Hz), 6.92 (m, 4H), 7.06 (m, 1H), 7.20–7.41 (m, 12H), 7.57 (s, 1H), 10.5 (bs, 1H), 10.6 (bs, 1H). $^{31}$PNMR (d6 DMSO) 0.45 (dd, JA=8.6 Hz, J=P–H=584 Hz).

The claims hereafter are to be construed to exclude any subject matter that, at the date of this invention, would not have been patentable under applicable statutory and judicial authority.

---

We claim:

1. A compound having the structure:

(1)

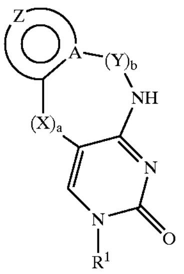

wherein $R^1$ is a binding partner, a linker or H;

a and b independently are 0 or 1, provided that the total of a and b is 0 or 1;

A is independently N or C;

X is independently S, O, —C(O)—, NH or $NCH_2R^6$;

Y is —C(O)—;

Z is taken together with A to form a 5- or 6-membered aryl or heteroaryl ring structure wherein the heteroaryl ring has a single O ring heteroatom, a single N ring heteroatom, a single S ring heteroatom, a single O and a single N ring heteroatom separated by a carbon, a single S and a single N ring heteroatom separated by a carbon, 2N ring heteroatoms separated by a carbon atom, or 3 N ring heteroatoms at least two of which are separated by a carbon atom, and wherein the aryl or heteroaryl ring carbon atoms are unsubstituted or at least 1 nonbridging ring carbon atom is substituted with $R^6$ or =O;

$R^6$ is independently H, $C_1$–$C_6$ alkyl, $C_2$–$C_6$ alkenyl, $C_2$–$C_6$ alkynyl, $NO_2$, $N(R^3)_2$, C≡N or halo, or an $R^6$ is taken together with an adjacent $R^6$ to complete a ring containing 5 or 6 ring atoms;

$R^3$ is a protecting group or H;

and provided that where a is 0, b is 1 and $R^1$ is

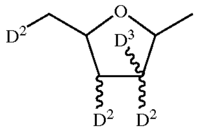

in which $D^2$ is independently hydroxyl, protected hydroxyl, mono, di or triphosphate, or an oligodeoxyribonucleotide otherwise containing only the bases A, G, T and C; and $D^3$ is H or OH;

then Z taken together with the A and carbon to which it is bound does not form an unsubstituted phenylene;

and tautomers, solvates and salts thereof.

2. The compound of claim 1 wherein $R^1$ is a linker and said linker has a substituent group which is hydroxyl, $O—P(=O)(O^-)_2$ or $—P(=O)(O^-)_2$.

3. The compound of claim 1 wherein $R^1$ is a linker selected from the group consisting of:

$E—CHR^7—R^{11}—(CH_2)_{m1}—C(R^8)((CH_2)_{m1}(R^9))—(CH_2)_{m1}—(CH_2)_{m1}—$, $E—Q—C_6H_4—CH_2—$;

$E—CHR^7—O—CHR^7—O—CHR^7—$, $E—CHR^7—(CHR^{13})_{m1}—CHR^{14}—R^{10}—$, $H(CH_2)_{m1}CH(COOR^{20})(CH_2)_{m1}—$ (27)

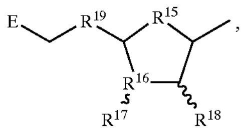

, (28)

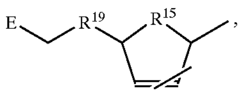

, and

-continued (29)

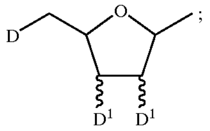

D is an oligonucleotide coupling group;

$D^1$ is independently F, H, O-alkyl, S-alkyl or an oligonucleotide coupling group, but only one $D^1$ is a coupling group;

Q is independently $—C(R^{12})_2—CH_2—$, $C(R^{12})_2—O—$, $—CR^{12}═CR^{12}—$, or —C≡C—;

$R^7$ is independently H or $C_1$–$C_4$ alkyl;

$R^8$ is H or $C_1$–$C_4$ alkyl, $C_2$–$C_4$ alkenyl or azidomethyl;

$R^9$ is halo, H or $OR^{20}$ $R^{10}$ is O, $CH_2$ or a covalent bond;

$R^{11}$ is O, S, $CH_2$, CHF or $CF_2$;

$R^{12}$ is independently H or halogen;

$R^{13}$ is H, halogen, $OR^{20}$, $CH_3$, $CH_2OR^{20}$ or $C_3$–$C_6$ acyloxyalkyl;

$R^{14}$ is H, halogen, $OR^{20}$, $CH_3$, $CH_2OR^{20}$, $C_3$–$C_6$ acyloxymethyl, or $C_2$–$C_6$ acyloxy, $R^{15}$ is $CH_2$, CHF or O;

$R^{16}$ is CH or S, provided that when $R^{19}$ is O or S, or $R^{15}$ is $CH_2$, then $R^{16}$ is not S;

$R^{17}$ is H, $OR^{20}$, halogen, $N_3$, $C_1$–$C_4$ alkyl or $C_1$–$C_4$ alkoxy or is absent when $R^{16}$ is S;

$R^{18}$ is H, $OR^{20}$, halogen, $N_3$, $C_1$–$C_4$ alkyl or $C_1$–$C_4$ alkoxy;

$R^{19}$ is O, S, $CH_2$, CHF or $CF_2$;

$R^{20}$ is H or a protecting group;

m1 is independently 0 or an integer from 1 to 4; and

E is OH, $OR^{20}$, $O—P(═O)(O^-)_2$, and $—P(═O)(O^-)_2$.

4. The compound of claim 1 wherein $R^1$ is H; $HOCH(CHR^{13})CH_2—$; $ECH_2OCH(CHR^{13})CH_2—$; or

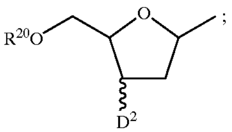

E is OH, $OR^{20}$, $O—P(═O)(O^-)_2$, and $—P(═O)(O^-)_2$;

$D^2$ is independently F, H, O-alkyl, S-alkyl or an oligonucleotide coupling group;

$R^{13}$ is H, halogen, $OR^{20}$, $CH_3$, $CH_2OR^{20}$ or $C_3$–$C_6$ acyloxyalkyl; and $R^{20}$ is H or a protecting group.

5. The compound of claim 1 wherein Z is (18)

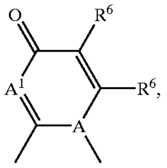

-continued (19)

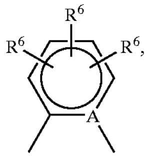

or (20)

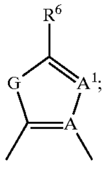

$A^1$ is N or $CR^6$; and

G is CH, S, O or $NR^4$; and $R^4$ is H or $C_1$–$C_6$ alkyl.

6. The compound of claim 5 wherein Z is (21)

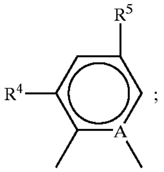

$R^4$ is H or $C_1$–$C_6$ alkyl; and $R^5$ is H, $NO_2$ or $C_1$–$C_6$ alkyl.

7. The compound of claim 5 wherein Z is (22)

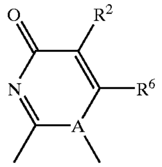

$R^2$ is $C_1$–$C_6$ alkyl and $R^6$ is H.

8. The compound of claim 5 wherein Z is (23)

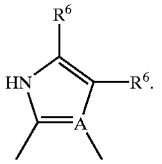

9. The compound of claim 5 wherein adjacent $R^6$ are taken together to complete a phenyl, thiazole, imidazole, oxazole, pyridine or pyrimidine ring.

10. The compound of claim 5 wherein G is S, O or $NR^4$.

11. The compound of claim 5 wherein Z is (24)

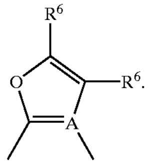

12. The compound of claim 5 wherein Z is (25)

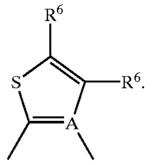

13. The compound of claim 1 wherein b is 0.

14. The compound of claim 1 wherein a is 1 and X is O.

15. The compound of claim 1 wherein b is 1 and a is 0.

16. The compound of claim 1 wherein A is C.

17. The compound of claim 1 wherein A is N.

18. The compound of claim 5 wherein A is N.

19. The compound of claim 5 wherein A is CH.

20. The compound of claim 1 wherein Z together with A and the carbon to which Z is bound completes a aryl ring containing 6 ring atoms.

21. The compound of claim 20 wherein the aryl ring contains a nonbridging ring carbon atom which is singly substituted with $R^6$.

22. The compound of claim 1 wherein Z together with the A and carbon to which Z is bound completes a heteroaryl residue which has 1 ring N atom; 2 ring N atoms; 1 ring oxygen atom, 1 ring nitrogen and 1 ring sulfur atom separated by at least 1 carbon atom; or 3 ring N atoms at least two of which are separated by at least 1 carbon atom.

23. The compound of claim 1 wherein Z together with the A and carbon to which Z is bound completes a heteroaryl ring consisting of 5 atoms, one of which is N.

24. The compound of claim 1 wherein A is C, b is 0, a is 1, and X is O, C(O) or S.

25. The compound of claim 1 wherein a and b are both 0.

26. The compound of claim 1 wherein A is N, b is 0, a is 1 and X is O.

27. The compound of claim 24 wherein Z together with A and the carbon to which Z is bound completes an aryl ring consisting of an unsubstituted aryl ring or an aryl ring substituted with $R^6$.

28. The compound of claim 25 wherein A is C and Z together with A and the carbon to which Z is bound completes an unsubstituted pyridine ring or is a pyridine ring substituted with $R^6$.

29. The compound of claim 1 wherein a is 0, b is 1 and Y is C(O).

30. An oligomer having the structure (8)

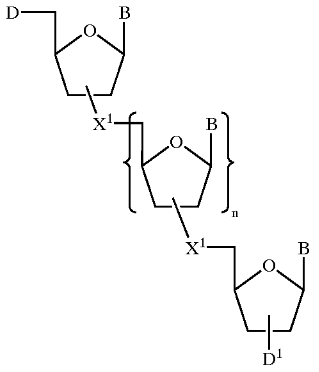

wherein

D is OH or blocked OH;

$D^1$ is an oligonucleotide coupling group or OH;

$X^1$ is independently a phosphodiester linkage or a phosphodiester substitute linkage bonded to the 2' or 3' position of a furanose ring, and the remaining 2' or 3' position is substituted with $R^{21}$;

$R^{21}$ is H, OH, F, —O-alkyl ($C_1$–$C_{12}$), —S-alkyl ($C_1$–$C_{12}$), $OC_3H_5$, or $SC_3H_5$;

n is an integer from 0 to 98; and

B is a purine or pyrimidine base provided that at least one B has the structure (30)

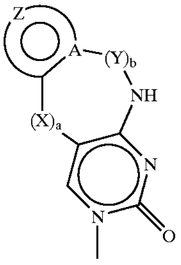

wherein a and b are 0 or 1 provided that the total of a and b is 0 or 1;

A is N or C;

X is S, O, —C(O)—, NH or $NCH_2R^6$;

Y is —C(O)—;

Z together with a and the carbon which Z is bound to form 5- or 6-membered aryl or heteroaryl ring structure wherein the heteroaryl ring has a single O ring heteroatom, a single N ring heteroatom, a single S ring heteroatom, a single O and a single N ring heteroatom separated by a carbon, a single S and a single N ring heteroatom separated by a carbon, 2N ring heteroatoms separated by a carbon atom, or 3 N ring heteroatoms at least two of which are separated by a carbon atom, and wherein the aryl or heteroaryl ring carbon atoms are unsubstituted or at least 1 nonbridging ring carbon atom is substituted with $R^6$ or =O;

$R^6$ is independently H, $C_1$–$C_6$ alkyl, $C_2$–$C_6$ alkenyl, $C_2$–$C_6$ alkynyl, $NO_2$, $N(R^3)_2$, C≡N or halo, or an $R^6$ is taken together with an adjacent $R^6$ to complete a ring containing 5 or 6 ring atoms;

$R^3$ is a protecting group or H; and provided that where a is 0, b is 1 and $R^1$ is

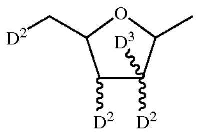

in which $D^2$ is independently hydroxyl, protected hydroxyl, mono, di or triphosphate, or an oligodeoxyribonucleotide otherwise containing only the bases A, G, T and C; and $D^3$ is H or OH;

then Z is not unsubstituted phenylene;

and tautomers, solvates and salts thereof.

31. The oligonucleotide of claim 30 wherein $X^1$ is —P(S)($O^-$)—, —P(O)($O^-$)—, —P(ME)(O)—, or —P(ME)(S)—.

32. The oligomer of claim 30 wherein Z together with A and the carbon to which Z is bound is (18)

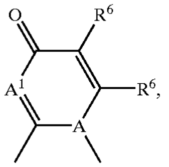

(19)

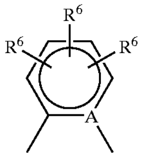

, or (20)

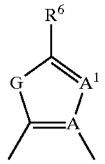

;

$A^1$ is N or $CR^6$;

G is CH, S, O or $NR^4$; and $R^4$ is H or $C_1$–$C_6$ alkyl;

and the tautomers, solvates and salts thereof.

33. The oligomer of claim 30 wherein Z together with A and the carbon to which Z is bound is (21)

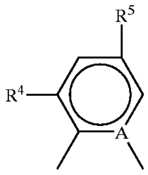

;

$R^4$ is H or $C_1$–$C_6$ alkyl; and $R^5$ is H, $NO_2$ or $C_1$–$C_6$alkyl.

34. The oligomer of claim 30 wherein Z together with A and the carbon to which Z is bound is (22)

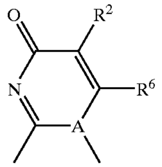

$R^2$ is $C_1$–$C_6$ alkyl and $R^6$ is H.

35. The oligomer of claim 30 wherein Z together with A and the carbon to which Z is bound is (23)

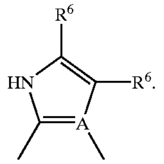

36. The oligomer of claim 30 wherein adjacent $R^6$ are taken together to form phenyl, thiazole, imidazole, oxazole, pyridine or pyrimidine radicals.

37. The oligomer of claim 30 wherein Z together with A and the carbon to which Z is bound is (24)

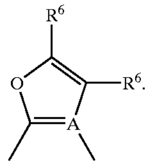

38. The oligomer of claim 30 wherein Z together with A and the carbon to which Z is bound is (25)

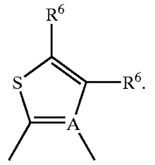

39. The oligomer of claim 30 containing from 2 to about 30 nucleotide units.

40. The oligomer of claim 30 wherein $R^{21}$ is H, OH, —O-allyl, —O-methyl, —O-ethyl or —O-propyl.

41. The oligomer of claim 30 wherein adjacent B groups have substructure (30).

42. The oligomer of claim 30 wherein bases other than substructure (30) consist of naturally-occurring nucleotide bases.

43. The oligomer of claim 30 wherein n is 0 to 20.

44. The oligomer of claim 30 wherein $D^1$ is an H-phosphonyl group, a methylphosphonamidityl group, a β-cyanoethylphosphoramidityl group or an alkylphosphoramidityl group.

45. The oligomer of claim 30 wherein D is OH, —$PO_3$, dimethoxytrityl-O or monomethoxytrityl-O.

46. The oligomer of claim 30 wherein a single B group having substructure (30) is located at the 5' or 3' end of the oligomer.

47. The oligomer of claim 30 wherein at least one B is 5-(1-propynyl) cytosinyl or uracilyl.

* * * * *

UNITED STATES PATENT AND TRADEMARK OFFICE

CERTIFICATE OF CORRECTION

PATENT NO. : 6,617,437 B1 
DATED : September 9, 2003
INVENTOR(S) : Mark Matteucci It is certified that error appears in the above-identified patent and that said Letters Patent is hereby corrected as shown below:

Title page,
Item 75], Inventors, please delete "Kuei-Ying" and insert therefor -- Kuei-Yuing --;

Column 32,
Line 51, please insert -- $R^{10}$ -- after "$(CH_2)_{m1}$-"
Line 65, please replace " 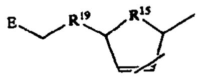 " with -- 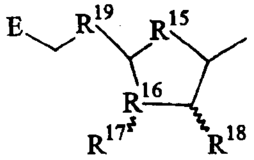 --;

Column 36,
Line 51, please delete "a" and insert therefor -- A --.

Signed and Sealed this

Twenty-fourth Day of August, 2004

Jon W. Dudas

JON W. DUDAS
*Director of the United States Patent and Trademark Office*

SEQUENCE LISTING

```
<160> NUMBER OF SEQ ID NOS: 3

<210> SEQ ID NO 1
<211> LENGTH: 15
<212> TYPE: RNA
<213> ORGANISM: Artificial Sequence
<220> FEATURE:
<223> OTHER INFORMATION: Synthetic Oligoribonucleotide

<400> SEQUENCE: 1

agagggagag aaaaa                                                    15


<210> SEQ ID NO 2
<211> LENGTH: 15
<212> TYPE: DNA
<213> ORGANISM: Artificial Sequence
<220> FEATURE:
<223> OTHER INFORMATION: Synthetic Oligonucleotide
<221> NAME/KEY: misc_feature
<222> LOCATION: (4)..(6)
<223> OTHER INFORMATION: N = 5-Propyne dC, Benzene Tricyclic dC,
      2-Pyridine Tricyclic dC, Phenathiazine Tricyclic dC, Phenoxazine
      Tricyclic dC, Phenoxazine di-methyl Tricyclic dC, or Phenoxazine
      Tricyclic dC

<400> SEQUENCE: 2

tctnnntctc ttttt                                                    15


<210> SEQ ID NO 3
<211> LENGTH: 15
<212> TYPE: DNA
<213> ORGANISM: Artificial Sequence
<220> FEATURE:
<223> OTHER INFORMATION: Synthetic Oligonucleotide
<221> NAME/KEY: misc_feature
<222> LOCATION: (2)..(2)
<223> OTHER INFORMATION: N = cytidine, 5-Propyne dC, Benzene Tricyclic
      dC, 2-Pyridine Tricyclic dC, Phenathiazine Tricyclic dC,
```

-continued

```
      Phenoxazine Tricyclic dC, Phenoxazine di-methyl Tricyclic dC, or
      Phenoxazine Tricyclic dC
<221> NAME/KEY: misc_feature
<222> LOCATION: (4)..(6)
<223> OTHER INFORMATION: N = cytidine, 5-Propyne dC, Benzene Tricyclic
      dC, 2-Pyridine Tricyclic dC, Phenathiazine Tricyclic dC,
      Phenoxazine Tricyclic dC, Phenoxazine di-methyl Tricyclic dC, or
      Phenoxazine Tricyclic dC
<221> NAME/KEY: misc_feature
<222> LOCATION: (8)..(8)
<223> OTHER INFORMATION: N = cytidine, 5-Propyne dC, Benzene Tricyclic
      dC, 2-Pyridine Tricyclic dC, Phenathiazine Tricyclic dC,
      Phenoxazine Tricyclic dC, Phenoxazine di-methyl Tricyclic dC, or
      Phenoxazine Tricyclic dC
<221> NAME/KEY: misc_feature
<222> LOCATION: (10)..(10)
<223> OTHER INFORMATION: N = cytidine, 5-Propyne dC, Benzene Tricyclic
      dC, 2-Pyridine Tricyclic dC, Phenathiazine Tricyclic dC,
      Phenoxazine Tricyclic dC, Phenoxazine di-methyl Tricyclic dC, or
      Phenoxazine Tricyclic dC

<400> SEQUENCE: 3

tntnnntntn ttttt                                                       15
```